(12) United States Patent
Krauter et al.

(10) Patent No.: US 8,376,942 B2
(45) Date of Patent: Feb. 19, 2013

(54) ARTICULATION MECHANISM FOR A VAGINAL SPECULUM

(75) Inventors: Allan I. Krauter, Skaneateles, NY (US); Dale C. Saddlemire, Cortland, NY (US); Michael T. McMahon, Syracuse, NY (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1506 days.

(21) Appl. No.: 11/913,426

(22) PCT Filed: May 8, 2006

(86) PCT No.: PCT/US2006/017736
§ 371 (c)(1),
(2), (4) Date: Nov. 2, 2007

(87) PCT Pub. No.: WO2006/122031
PCT Pub. Date: Nov. 16, 2006

(65) Prior Publication Data
US 2009/0275803 A1    Nov. 5, 2009

Related U.S. Application Data

(60) Provisional application No. 60/678,260, filed on May 6, 2005, provisional application No. 60/735,576, filed on Nov. 10, 2005.

(51) Int. Cl.
*A61B 1/32* (2006.01)
(52) U.S. Cl. .................................. 600/222; 600/220
(58) Field of Classification Search .................. 600/214, 600/220–222, 225, 226; 606/205–208
See application file for complete search history.

(56) References Cited

U.S. PATENT DOCUMENTS

| | | |
|---|---|---|
| 3,978,850 A | 9/1976 | Moore et al. |
| 3,985,125 A | 10/1976 | Rose |
| 4,010,740 A | 3/1977 | Littorin |
| 4,156,424 A | 5/1979 | Burgin |
| 4,202,324 A | 5/1980 | Alison |
| 4,263,898 A | 4/1981 | Wannag |
| 4,263,899 A | 4/1981 | Burgin |
| 4,432,351 A | 2/1984 | Hoary |
| D274,356 S | 6/1984 | Riedell |
| 4,566,439 A | 1/1986 | Burgin |
| 4,597,383 A | 7/1986 | VanDerBel |
| 4,766,887 A | 8/1988 | Cecil, Jr. et al. |
| D299,532 S | 1/1989 | Cecil, Jr. et al. |
| 4,854,300 A | 8/1989 | Corbo |
| 4,884,559 A | 12/1989 | Collins |
| 4,905,670 A | 3/1990 | Adair |
| 4,971,036 A | 11/1990 | Collins |
| 4,994,070 A | 2/1991 | Waters |
| 5,018,507 A | 5/1991 | Montaldi |
| 5,026,368 A | 6/1991 | Adair |
| 5,052,372 A | 10/1991 | Shapiro |
| 5,072,720 A | 12/1991 | Francis et al. |
| 5,081,983 A | 1/1992 | Villalta |
| 5,143,054 A | 9/1992 | Adair |
| 5,174,278 A | 12/1992 | Babkow |
| 5,179,937 A | 1/1993 | Lee |
| 5,231,973 A | 8/1993 | Dickie |
| 5,318,010 A | 6/1994 | Lundberg |

(Continued)

FOREIGN PATENT DOCUMENTS
WO    WO 2006/122031 A2    11/2006

*Primary Examiner* — Andrew Yang

(57) ABSTRACT

An articulation mechanism for a vaginal speculum enables selective relative movement between an upper blade member and a lower blade member to affect vertical and angular spacing. The mechanism selectively enables quiet or clicking articulation according to at least one version.

21 Claims, 18 Drawing Sheets

U.S. PATENT DOCUMENTS

| | | | |
|---|---|---|---|
| 5,329,938 A | 7/1994 | Lonky | |
| 5,377,667 A | 1/1995 | Patton et al. | |
| 5,499,964 A * | 3/1996 | Beck et al. | 600/220 |
| 5,505,690 A | 4/1996 | Patton et al. | |
| 5,509,893 A | 4/1996 | Pracas | |
| 5,704,901 A | 1/1998 | Meister | |
| 5,718,665 A | 2/1998 | Stubbs | |
| 5,722,983 A | 3/1998 | Van Der Weegen | |
| 5,743,852 A | 4/1998 | Johnson | |
| 5,785,648 A | 7/1998 | Min | |
| 5,842,974 A | 12/1998 | Stubbs | |
| 5,868,668 A | 2/1999 | Weiss | |
| 5,873,820 A | 2/1999 | Norell | |
| 5,916,150 A | 6/1999 | Sillman | |
| 5,916,151 A | 6/1999 | Charters | |
| 5,997,474 A | 12/1999 | Batchelor | |
| 6,004,265 A | 12/1999 | Hsu et al. | |
| 6,024,696 A | 2/2000 | Hoftman et al. | |
| 6,024,697 A | 2/2000 | Pisarik | |
| 6,048,308 A | 4/2000 | Strong | |
| 6,096,046 A | 8/2000 | Weiss | |
| 6,280,379 B1 | 8/2001 | Resnick | |
| 6,342,036 B1 | 1/2002 | Cooper et al. | |
| 6,354,995 B1 | 3/2002 | Hoftman et al. | |
| 6,364,832 B1 | 4/2002 | Propp | |
| 6,379,299 B1 | 4/2002 | Borodulin et al. | |
| 6,394,950 B1 | 5/2002 | Weiss | |
| 6,416,467 B1 | 7/2002 | McMillin et al. | |
| 6,432,048 B1 | 8/2002 | Francois | |
| 6,432,049 B1 | 8/2002 | Banta et al. | |
| 6,450,952 B1 | 9/2002 | Rioux et al. | |
| 6,569,091 B2 | 5/2003 | Diokno et al. | |
| 6,595,917 B2 | 7/2003 | Nieto | |
| 6,669,654 B2 | 12/2003 | Diokno et al. | |
| 6,712,761 B2 | 3/2004 | Borodulin et al. | |
| 2002/0022771 A1 | 2/2002 | Diokno et al. | |
| 2002/0115910 A1 | 8/2002 | Diokno et al. | |
| 2002/0156350 A1 | 10/2002 | Nieto | |
| 2002/0177791 A1 | 11/2002 | Diokno et al. | |
| 2002/0177842 A1 | 11/2002 | Weiss | |
| 2003/0069477 A1 | 4/2003 | Raisman et al. | |
| 2003/0105387 A1 | 6/2003 | Frumovitz et al. | |
| 2003/0176722 A1 * | 9/2003 | Inoki et al. | 558/418 |
| 2003/0176772 A1 | 9/2003 | Yang | |
| 2003/0225313 A1 | 12/2003 | Borodulin et al. | |
| 2004/0054260 A1 | 3/2004 | Klaassen et al. | |
| 2004/0133077 A1 | 7/2004 | Obenchain et al. | |
| 2004/0184288 A1 | 9/2004 | Bettis | |
| 2004/0186355 A1 | 9/2004 | Strong et al. | |

* cited by examiner

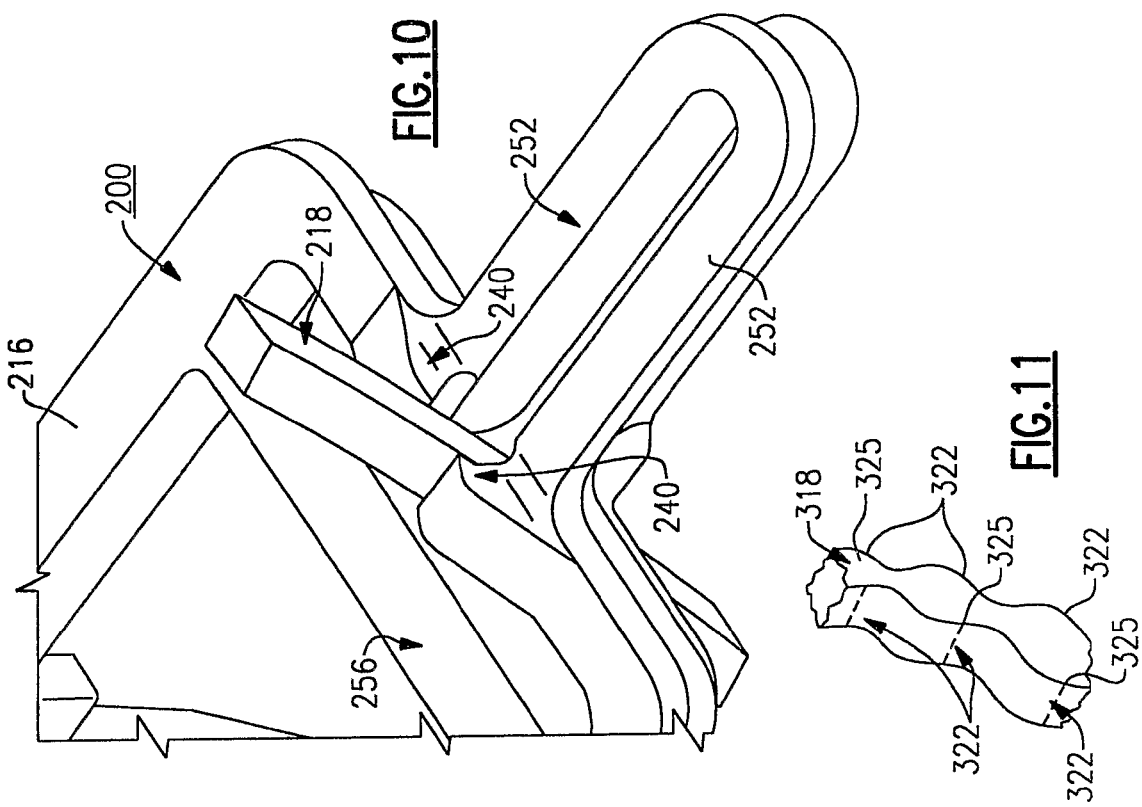
FIG. 10
FIG. 11
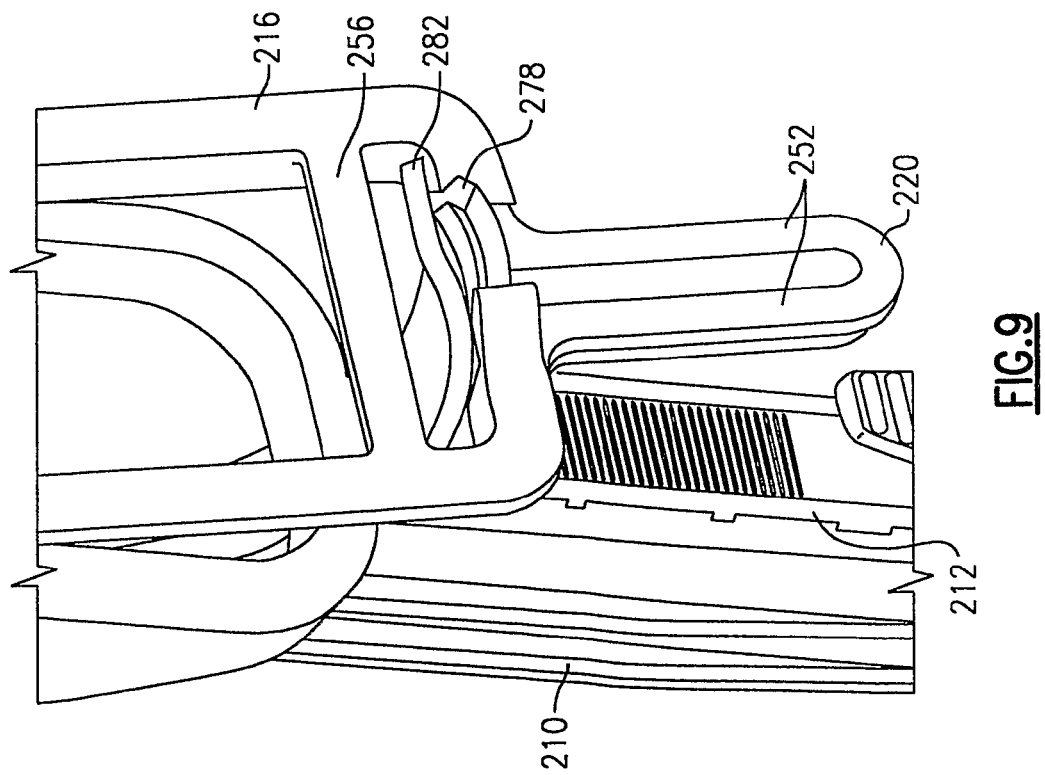
FIG. 9

US 8,376,942 B2

ARTICULATION MECHANISM FOR A VAGINAL SPECULUM

CROSS REFERENCE TO RELATED APPLICATIONS

This application is based upon and claims priority under 35 USC §119 of PCT/US2006/017736, filed May 8, 2006, which is based upon U.S. Ser. No. 60/678,260, entitled: ARTICULATION MECHANISM FOR A VAGINAL SPECULUM, filed May 6, 2005 and U.S. Ser. No. 60/735,576, entitled: ILLUMINATED VAGINAL SPECULUM ASSEMBLY, filed Nov. 10, 2005. The entire contents of each above noted application is herein incorporated by reference.

FIELD OF THE INVENTION

This invention relates to the field of medical diagnostic instruments, and in particular to a vaginal speculum having an improved blade articulation mechanism.

BACKGROUND OF THE INVENTION

Vaginal specula, such as those that are manufactured and sold by Welch Allyn, Inc. of Skaneateles Falls, N.Y., among others are typically characterized by a pair of blade members that are inserted into the vaginal cavity of a patient. A blade articulation (angulation) mechanism is used to selectively vary the angular spacing or angular separation of the blade members to dilate the cavity for examination purposes. The upper blade member is pivotally attached to the speculum by means of a slide or yoke member wherein the blade articulation mechanism for these prior art specula typically includes a curved arm extending rearwardly from the slide member, the curved arm having a set of serrated ratchet teeth on a proximal side thereof that are engaged by an engagement tooth provided on a downwardly extending lever of the upper blade. The user pushes downwardly upon a tab portion of the lever in order to lock the upper blade member in a selected articulation (angulation) position wherein the angular separation of the blade members is required in order to suitably dilate the vaginal opening of a patient for examination purposes.

The above speculum can also include a similar ratchet mechanism which is provided on the slide member, and a downwardly extending handle portion of the speculum in order to provide vertical elevation (translation) adjustment of the upper blade member relative to the lower blade member.

One problem with presently known articulation mechanisms, as described above, is that the audible "clicking" sounds associated with the engagement tooth of the lever of the upper blade member and the serrated ratchet teeth of the member arm of the above specula can be unsettling to the patient. This problem can be distracting, and depending on the patient, traumatic in some instances.

Conversely, the audible clicking sounds produced by present speculum articulation mechanisms also provide a benefit for some physicians who are utilizing the apparatus in order to define a predetermined angular spacing, based on the number of audible clicks that are heard. As a result, there are reasons to provide an articulation mechanism that can selectively, but not necessarily, provide quieter operation, depending on the user.

Another problem that has been noted is that quite often a medical glove can become snagged or otherwise caught between the engaged teeth of the present articulation mechanism. This problem can cause tearing of the glove, creating a potential contamination issue, or can otherwise impair an examination. An additional problem that has been noted is that the predetermined number of discrete articulation positions may be limiting to the physician. In some instances, there may be a need to provide an articulation mechanism capable to being set to an unlimited number of possible positions, thereby enabling continuous operation. Articulation mechanisms are presently available to enable continuous operation, but none of these mechanisms enable selectivity by the user between discrete and continuous modes of operation. A further problem that has been noted is that the prior art specula do not allow articulation (angulation) without automatic locking of the mechanism. Some users prefer to control this articulation with one hand throughout the medical procedure being conducted.

It is therefore a general need in the field to provide a blade articulation system for a vaginal speculum that is reliable, but which is quieter in terms of its operation. It is yet another general desire to produce an articulation mechanism for a vaginal speculum that does not necessarily have to rely upon a predetermined number of discrete stops (i.e., articulation positions) for purposes of its operation, but rather can selectively perform continuously through an infinite number of positions over a specified range.

SUMMARY OF THE INVENTION

Therefore and according to one aspect, there is provided a vaginal speculum including an upper blade member, a lower blade member and an articulation mechanism causing relative movement between the upper blade and the lower blade member. According to this aspect, the articulation mechanism includes means for enabling the mechanism to selectively operate in one of at least one mode of operation. More particularly, the articulation mechanism enables the upper and lower blade members to be selectively angularly articulated according at least one embodiment in at least two forms of a passive mode. According to another embodiment, the at least one mode is an active mode. Active mode, passive mode and the two forms of passive mode are defined herein below.

In one version, a slide member includes a rearwardly extending curved arm having at least one arm engagement feature and the upper blade member includes a downwardly extending lever portion having at least one lever engagement feature. The lever portion further includes, according to this aspect, a user-actuated element for selectively angulating the upper and lower blade members between two forms of a passive mode.

In one version, the at least one lever engagement feature includes an engagement tooth and said at least one arm engagement feature includes a series of serrated teeth wherein movement of said user-actuated element in a first form of passive mode causes direct engagement of said engagement tooth with said series of serrated teeth and in which movement of said user-actuated element in a second form of passive mode causes a portion of said user-actuated element to engage said curved arm, permitting quiet angulation.

According to one embodiment, the at least one arm engagement feature further includes a proximal ridge onto which the user-actuated element engages in lieu of said series of serrated teeth in said second form of passive mode. As such, the first form of passive mode enables angular articulation over a discrete number of articulation positions in the conventional manner and the second form of passive mode produces quiet operation over the range of articulation positions.

In one embodiment, the slide member includes a rearwardly extending curved arm having at least two arm engagement features and the upper blade member having a downwardly extending lever portion including an engagement portion. According to this embodiment, the at least two arm engagement features includes a series of serrated teeth disposed along a bottom surface of the curved arm and an axial ridge disposed along the bottom surface of the curved arm. Engagement of the axial ridge by a user permits the curved arm to be moved out of the engagement portion of the lever portion to permit selective engagement of one of the series of said serrated teeth with the lever portion to effect angular articulation between the upper blade member and the lower blade member.

According to another aspect, there is provided an articulation mechanism for a vaginal speculum, the speculum including an upper blade member, a lower blade member and a slide member permitting pivotal attachment of said upper blade member relative to the lower blade member. The articulation mechanism includes a lever portion extending from the upper blade member, the lever portion having an engagement portion for engaging an outwardly extending curved arm of the slide member. The engagement portion of the lever portion includes at lease one pair of side tongues sized for retaining the curved arm therebetween.

According to one version thereof, the curved arm can include a series of laterally provided undulations to permit the engagement of the at least one pair of side tongues therein, and providing a series of predefined discrete settings for the articulation mechanism.

According to yet another version, there is provided an articulation mechanism for a vaginal speculum, said speculum including an upper blade member, a lower blade member and a slide member permitting pivotal attachment of said upper blade member relative to said lower blade member, said articulation mechanism comprising a lever portion extending from said upper blade member, said lever including an engagement portion and a tab, said engagement portion being sized to engage said curved arm, said curved arm including a plurality of protrusions wherein movement of said lever permits said curved arm to pass through said engagement portion without contact therewith and in which a subsequent movement of said curved arm causes said engagement portion to lock into engagement with at least one protrusion.

According to yet another version, there is provided an articulation mechanism for a vaginal speculum, said speculum including an upper blade member, a lower blade member and a slide member permitting pivotal attachment of said upper blade member, said articulation mechanism including a lever portion downwardly extending from a proximal end of said upper blade member, said lever portion including an engagement portion sized for engaging a curved arm of said slide member, said curved arm including a series of spaced engagement surfaces wherein movement of said lever portion in a first direction causes said curved arm to pass through said engagement portion without contact with said engagement surfaces and in which a subsequent second movement of said lever portion in a lateral direction causes engagement with at least one engagement surface of said curved arm.

In one variation, the engagement surfaces can be lateral protrusions provided in spaced relation on each side of the curved arm. In another variation, the engagement surfaces can be teeth provided on the proximal side of the slide member.

According to another aspect, there is provided a vaginal speculum comprising: an upper blade member; a lower blade member; and a slide member interconnecting said upper blade member and said lower blade member and permitting relative movement therebetween. Articulation means are further provided for varying the angular spacing between distal ends of the upper and lower blade members, the articulation means selectively permits the angular spacing to be varied discretely and over a continuous range of positions.

In one version, the upper blade member can include a downwardly formed lever portion, the lever portion including an engagement portion. The slide member, according to this version, includes an elongated member having an external thread, the elongated member being attached to the proximal side of said slide member. A rotatable cap member is engageable with the external thread of the elongated member and also with the engagement portion of said lever portion, the elongated member being connected to said slide member to permit disengagement and engagement of said rotatable cap member with said lever portion. As such, articulation can be provided either continuously over a range of positions by adjustment of the rotatable cap member or discretely by selectively lifting the elongated member out of the engagement portion of the lever portion.

According to yet another aspect, there is provided a vaginal speculum comprising an upper blade member including a downwardly extending lever portion and a bottom tab, a lower blade member, and a slide member pivotally interconnecting the proximal end of the upper blade member and the lower blade member. The lever portion according to this aspect includes at least one lever engagement feature and the slide member includes an outwardly extending curved arm having a least one lateral arm engagement feature engaged by the lever engagement feature for permitting angular articulation of the upper and lower blade members.

In one embodiment, the at least one lateral arm engagement feature includes a plurality of spaced lateral undulations and the at least one lever engagement feature includes at least one pair of spaced side tongues. The at least one pair of side tongues are defined by a spacing that is smaller than the width of said curved arm. The lateral undulations define pinch regions for the at least one lever engagement feature.

The at least one lateral arm engagement feature can include a flange extending along substantially the length of the curved arm, wherein the engagement features enable continuous operation over a range of articulation position such that the upper and lower blade members can be set selectively within a range of articulation positions.

In one embodiment, the lever portion includes a pair of flexible spaced legs that twist during motion of the at least one pair of side tongues.

In another embodiment, the outwardly extending curved arm is acted upon by a user to move said at least one pair of side tongues out of engagement with the at least one lever engagement feature and the bottom tab is acted upon by a user to move the at least one pair of side tongues into engagement with the at least one lateral arm engagement feature.

An advantage of herein described mechanism is that a vaginal speculum is provided that is quieter in use than previously known apparatus using an articulation mechanism according to at least one embodiment that can require relatively little modification to existing apparatus to incorporate.

Another advantage is that some of the embodiments described herein permit continuous operation of a vaginal speculum through an infinite number of articulation positions over a specified range.

Yet another advantage is that the speculum articulation mechanisms related herein can be utilized in a manner in which the user is not prone to having a medical glove snag on the apparatus during use.

Yet another advantage is that the herein described articulation mechanisms can be utilized by the user with either hand and that the majority of embodiments described herein are designed for one-hand operation.

These and other features and advantages will become readily apparent from the following General Description which should be read in conjunction with the accompanying drawings.

BRIEF DESCRIPTION OF THE DRAWINGS

FIG. 9 is a partial rear perspective view of a vaginal speculum illustrating an alternative version of an articulation mechanism in accordance with the third embodiment;

FIG. 10 is an assembled partial rear perspective view of the vaginal speculum of FIG. 8;

FIG. 11 depicts a curved arm in accordance with an alternative embodiment for an articulation mechanism such as shown in FIGS. 8 and 10;

GENERAL DESCRIPTION

The following description relates to various embodiments of blade articulation mechanisms for a specific vaginal speculum. It will be readily apparent to those of sufficient skill in the field, however, that certain variations and modifications are possible within the intended inventive scope. In addition, certain terms are used throughout the course of the following discussion in order to provide a framework for describing the mechanism in reference to the accompanying figures. These terms, however, unless indicated otherwise, should not be interpreted as limiting for purposes of the intended scope of the application.

Figure 1:
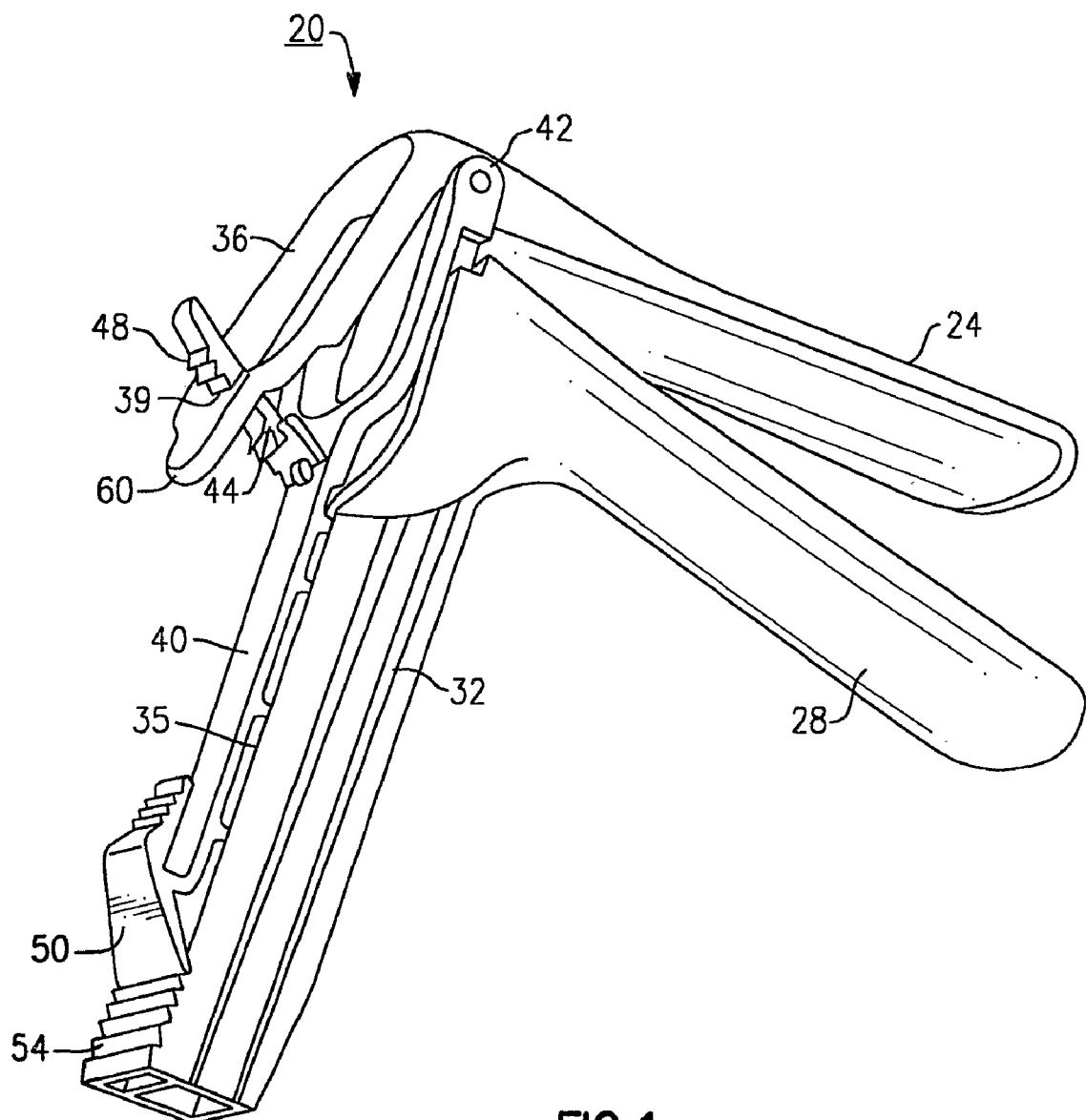
FIG. 1 is a perspective view of a prior art vaginal speculum.

Referring to FIG. 1 and for purposes of background, there is shown a perspective view of a prior art vaginal speculum. The speculum, herein referred to by reference numeral 20, includes an upper or top blade member 24 and a lower or bottom blade member 28. The speculum 20 further includes a hollow handle portion 32 that permits the inclusion of an illumination assembly (not shown). The upper blade member 24 is defined according to this embodiment by a molded plastic material, such as an acrylic or polystyrene, having an inwardly curved configuration, the proximal end of which includes a downwardly extending lever portion 36. The lower blade member 28 and the handle portion 32 are each integrally molded as a single component, also from a plastic material, such as clear acrylic or styrene, the lower blade member also including an elongate inwardly-curved configuration that corresponds with the curvature of that of the upper blade member 24. The hollow handle portion 32 extends downwardly from the proximal end of the lower blade member 28 and includes a vertical slot 35 for retaining a slide member 40, as described below.

The upper blade member 24 is attached to the remainder of the speculum 20 by means of the slide member 40, the slide member being attached for vertical movement in the vertical slot 35 of the hollow handle portion 32. More specifically, the slide member 40 includes an upper yoke section 42 extending to the upper blade member 24 that permits pivotal connection between the upper blade member 24 and the lower blade member 28. A single engagement tooth 50 is provided at the bottom of the slide member 40 for selectively engaging a set of serrated ratchet teeth 54 formed on a proximal side of the handle portion 32 directly beneath the vertical slot 35 to permit elevation (translation) of the upper blade member 24. The slide member 40 further includes a curved arm 44 that extends outwardly toward the proximal end of the speculum 20 and further includes a set of serrated ratchet teeth 48 on a proximal surface thereof, the serrated ratchet teeth being engaged by an single ramped engagement tooth 39 of the downwardly extending lever portion 36 of the upper blade member 24. Engagement of the single ramped engagement tooth 39 with the serrated ratchet teeth 48 defines a plurality of angular articulation positions.

In operation and in order to articulate the blade members, a user pushes downwardly upon a tab 60 immediately beneath the engagement tooth 39 of the lever portion 36 wherein the engagement tooth contacts the serrated ratchet teeth 48 of the curved arm 44. The teeth 48 are arranged relative to one another to create engagement with the tooth 39 of the lever portion 36 when the tab 60 is released by the user. Disengagement occurs by pushing upwardly on the proximal end of the curved arm 44, causing the curved arm 44 to disengage from the engagement tooth 39.

Figure 2:
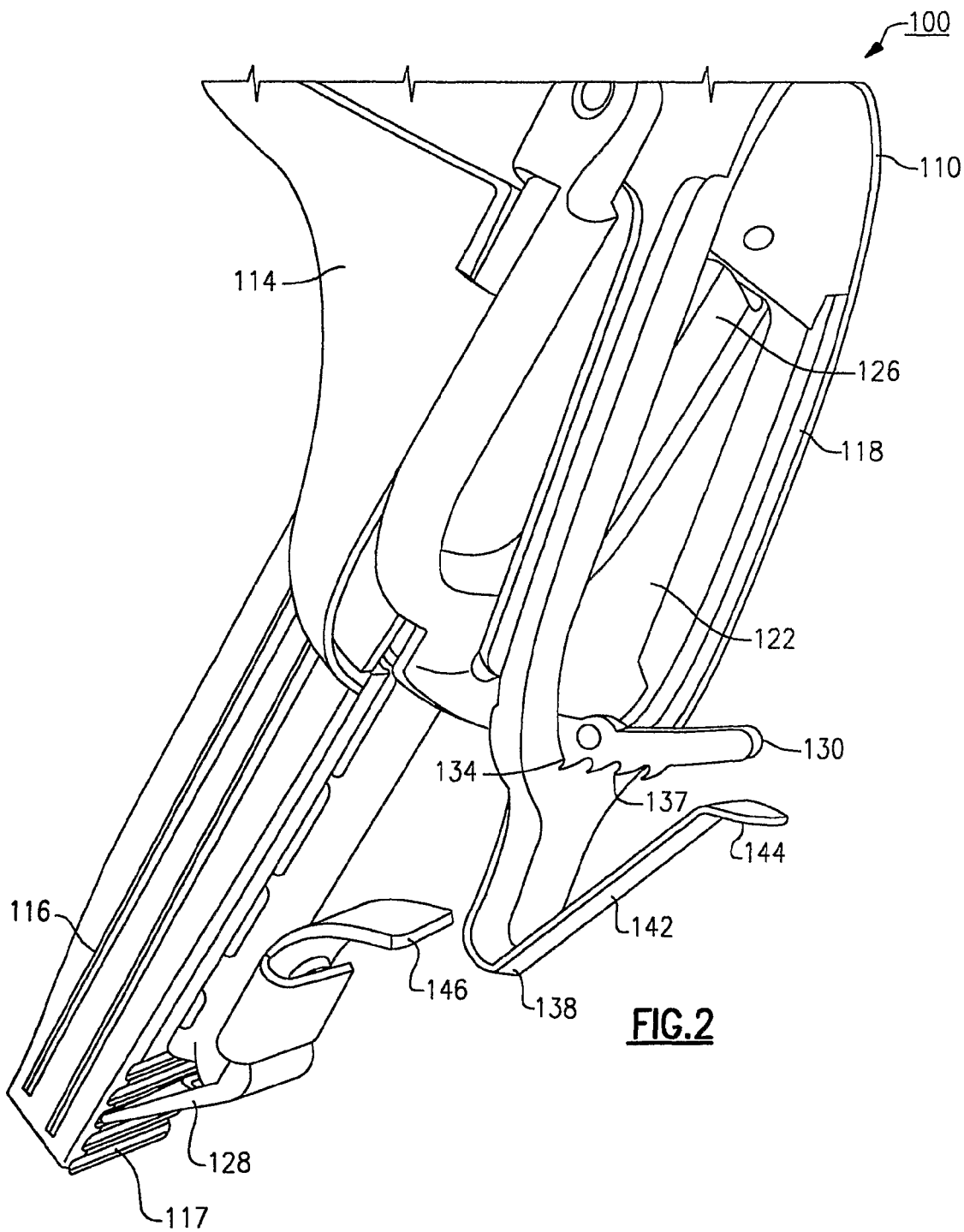
FIG. 2 is a rear perspective view of a vaginal speculum, including a blade articulation mechanism made in accordance with a first embodiment of the present invention.

With this background, reference is now made to FIG. 2 that illustrates an articulation mechanism according to a first embodiment. The following embodiment relates to an articulation mechanism for a vaginal speculum that can be selectively operated by a user in either at least one "passive" mode or an "active" mode. By "passive" mode, what is intended is that the articulation lock mechanism operates automatically when the tab 60, FIG. 1, is pushed downwardly. By "active" mode, what is intended is that the articulation mechanism is designed to lock only an action in addition to pushing the lever portion 36 downwards as performed by the user, such as will be detailed below. Passive mode as described herein can take two forms. The first form is that depicted according to the prior art embodiment of FIG. 1. In this first form, the serrated ratchet teeth are contacted during articulation so that an audible clicking sound is produced. In the second form, either no contact is made with the serrated ratchet teeth, or no serrated ratchet teeth are present on the curved arm of the slide member, such that no clicking sound is produced.

According to this specific embodiment, a speculum 100 includes a top or upper blade member 110 and a lower or bottom blade member 114. Each of the upper blade member 110 and lower blade member 114 is similar to that previously described in FIG. 1. To that end, the upper blade member 110 includes an angled downwardly extending lever portion 118 having an opening 122 and is pivotally attached to the top of a slide or yoke member 126 that is attached, as in the preceding, to a vertical slot formed in the handle portion 116 of the speculum 100.

The slide member 126, also as in the preceding, includes a curved arm 130 that engages the lever portion 118 of the upper blade member 110, the lever portion including a ramped engagement surface 134 for positive engagement with a set of serrated ratchet teeth 137 formed on the bottom facing or proximal side of the curved arm 130 so as to selectively adjust the articulation or angulation between the upper and lower blade members 110, 114. The slide member 126, also as in the preceding, includes a single tooth 128 that selectively engages a set of teeth 117 provided on the proximal side of the handle portion 116 to enable elevation.

According to this embodiment, the lever portion 118 of the upper blade member 110 is further provided with a lever extension 138. The lever extension 138 is made from a highly flexible material, such as a spring steel, or can also be suitably fabricated from plastic or other materials. For example, the lever extension 138 could be integrally molded from the same material as that of the upper blade member 110 or be separately attachable thereto. The lever extension 138 includes an angled engagement portion 142 that, when flexed by forward pressure from the user, permits the curved arm 130 to be pushed upwardly and moves the serrated ratchet teeth of the curved arm away from the ramped engagement surface 134 of the lever portion 118 of the upper blade member 110. The lever extension 138 further includes a flat portion 144 provided at the distal end thereof, the purpose of which will be described below.

In operation, the user can cause angular articulation of the mechanism according to this embodiment by pushing in a forward direction on the lever extension 138. If the user pushes on the lever extension 138 in the typical manner (i.e., by pushing on the lower end of the angled engagement portion 142 which is effectively equivalent to pushing on the tab 60, FIG. 1), the mechanism operates in the conventional way with the serrated ratchet teeth 137 of the curved arm 130 engaging directly against the ramped engagement surface 134 of the lever portion 118 of the upper blade member 110 in a discrete manner. Such passive mode, first form, operation produces the typical "clicking" sounds wherein the mechanism passively operates in this mode.

If, however, the user pushes upon the lever extension 138 towards the serrated ratchet teeth 137 of the curved arm 130 near the flat portion 144, the articulation mechanism operates in the passive mode, second (quiet) form, because the angled engagement portion 142 of the lever extension is caused to ride against the teeth. No noise and hence quiet operation is produced as a result in that the teeth 137 of the curved arm 130 are not engaged by the ramped engagement surface 134 of the lever portion 118. To selectively engage a tooth of the curved arm 130 and to lock the mechanism at the desired articulation angle, the user "rolls" the finger off of the lever extension 138, thereby allowing the single engagement tooth of the lever portion 118 of the upper blade member 110 to engage the selected ratchet tooth 137 of the curved arm 130. In order to subsequently disengage and close the upper blade 110 of the speculum 100, the user merely pushes up on the flat portion 144, which in turn pushes on the curved arm 130, disengaging the ratchet teeth 137 from the ramped engagement surface 134 of the lever portion 118.

As shown in FIG. 2, a similar angled or curved flexible curved extension 146 can also be similarly attached to the lower part of the slide member 126 for the elevation mechanism of the upper blade member 110. In terms of operation thereof and to provide vertical elevation, the user first pushes upwardly on the curved extension 146 and towards the patient. This causes the curved extension 146 to pull the tooth 128 away from the set of serrated handle teeth 117, utilizing the same principle described above. At the desired elevation, the finger of the user is "rolled off" this extension 146, thereby allowing the elevation ratchet to engage as is known.

Among the advantages of this described articulation mechanism are that the lever extension 138 prevents snagging of the medical glove by the ratchet teeth 137 of the curved arm 130. Another advantage is that the user can selectively operate this mechanism in either the first or second form of the passive mode, depending entirely on the selected action of the finger upon the lever extension 138 and/or curved extension 146.

Figure 3:
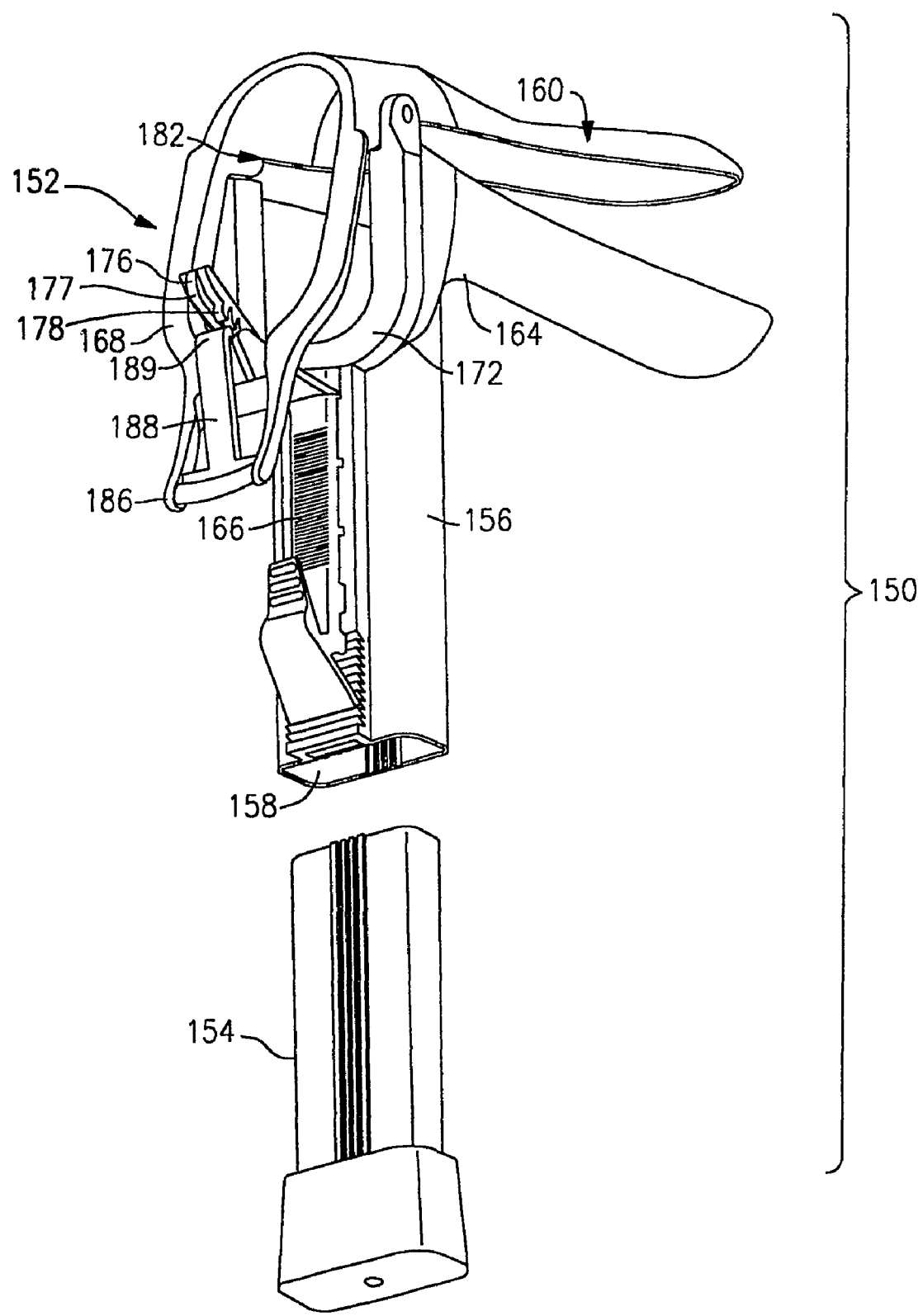
FIG. 3 is a view of a partially unassembled vaginal speculum assembly including an articulation mechanism that is manufactured in accordance with a second embodiment.
Figure 4:
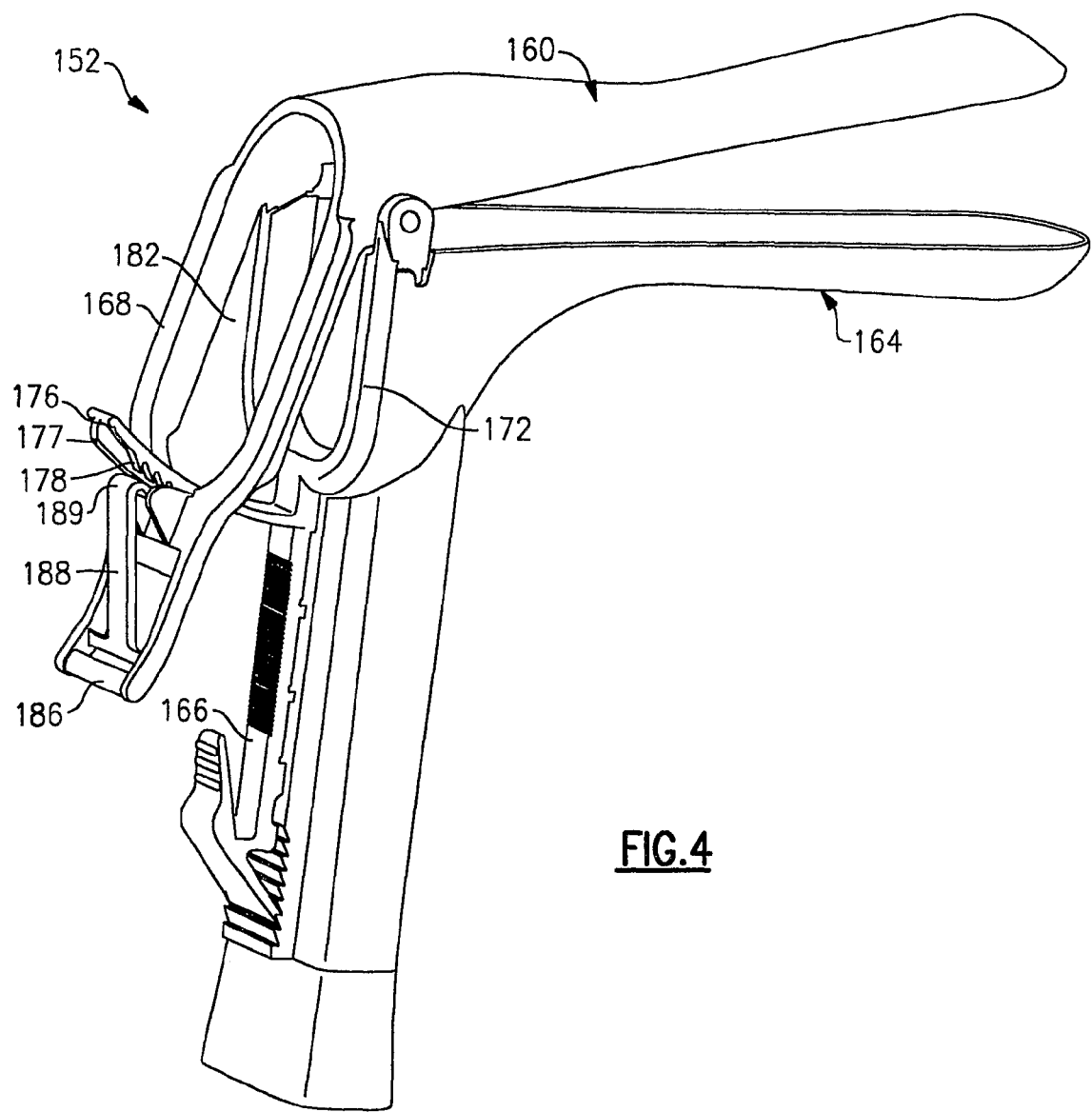
FIG. 4 is a side perspective view of the vaginal speculum assembly of FIG. 3.
Figure 5:
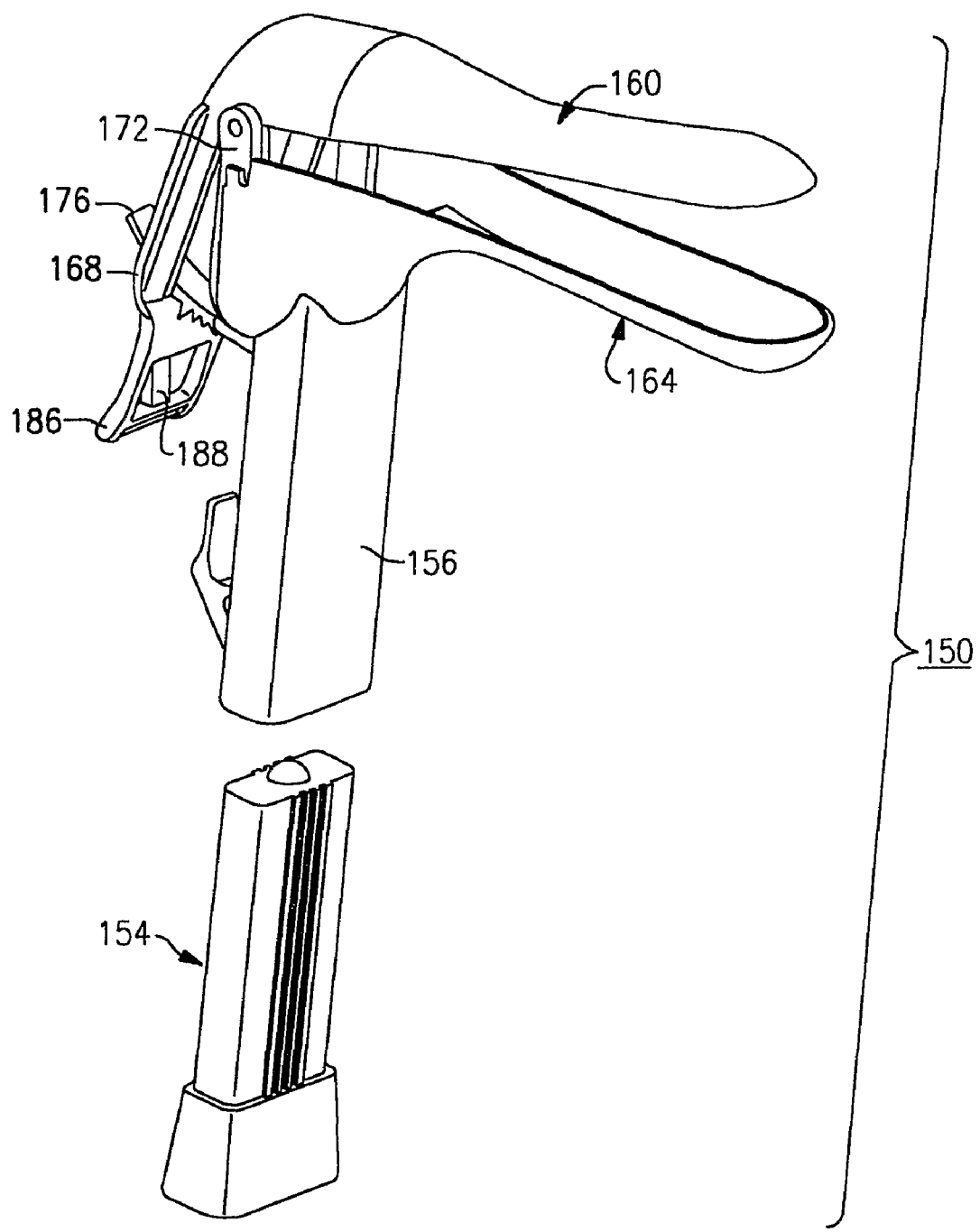
FIG. 5 is a front perspective view of the partially unassembled vaginal speculum assembly of FIGS. 3 and 4.

Referring now to FIGS. 3-5, there is shown a vaginal speculum assembly that is made in accordance with a second embodiment. According to this embodiment, the vaginal speculum apparatus 150 includes a disposable speculum 152 and a reusable illumination assembly 154 that is releasably attached to the speculum through a receiving cavity 158 provided in a hollow handle portion 156 thereof. In addition, the disposable speculum 152 is defined by an upper or top blade member 160, by a lower or bottom blade member 164, which integrally includes the hollow handle portion 156, and by a slide member 166. Each of the upper blade member 160 and lower blade member 164 is preferably formed from a durable transparent plastic material, such as acrylic or polystyrene, and in which each blade member is further defined by a trough-shaped elongate section or blade. The upper blade member 160 further includes a lever portion 168 extending downwardly at its proximal end thereof. The slide member 166, also preferably being made from a durable plastic material, though not necessarily transparent, further includes a forked upper portion or yoke 172 that pivotally receives the upper blade member 160, as well as a flexible projection 176 immediately beneath the yoke that extends rearward; that is, away from the hollow handle portion 156. The flexible projection 176 is curved in a concave configuration and includes a set of ratchet teeth 178 that are disposed along a bottom surface thereof.

The lever portion 168 includes an opening 182, defining an aperture through which the user can examine the patient through the upper and lower blade members 160, 164. The lever portion 168 also includes a bottom tab 186. Unlike the preceding, the bottom tab 186 includes a shield member 188 having an engagement end 189 for engaging a proximal ridge 177 that is provided on the flexible projection 176. According to this version, finger pressure on the shield member 188 causes the flexible projection 176 to flex away from the interior tab on the lever portion 168 until this pressure is released, the release of pressure causing a ratchet tooth to engage with the interior tab on the lever portion. In this passive mode, second form, operation, quiet articulation is achieved, wherein the patient is not startled or bothered by the noise typically generated between the interior tab and the ratchet teeth of conventional vaginal specula. Alternatively, finger pressure on the bottom tab 186 allows the user to angularly articulate the speculum 152 in a passive mode, first form, such that noise, similar to that of the prior art speculum, is produced.

Figure 6:
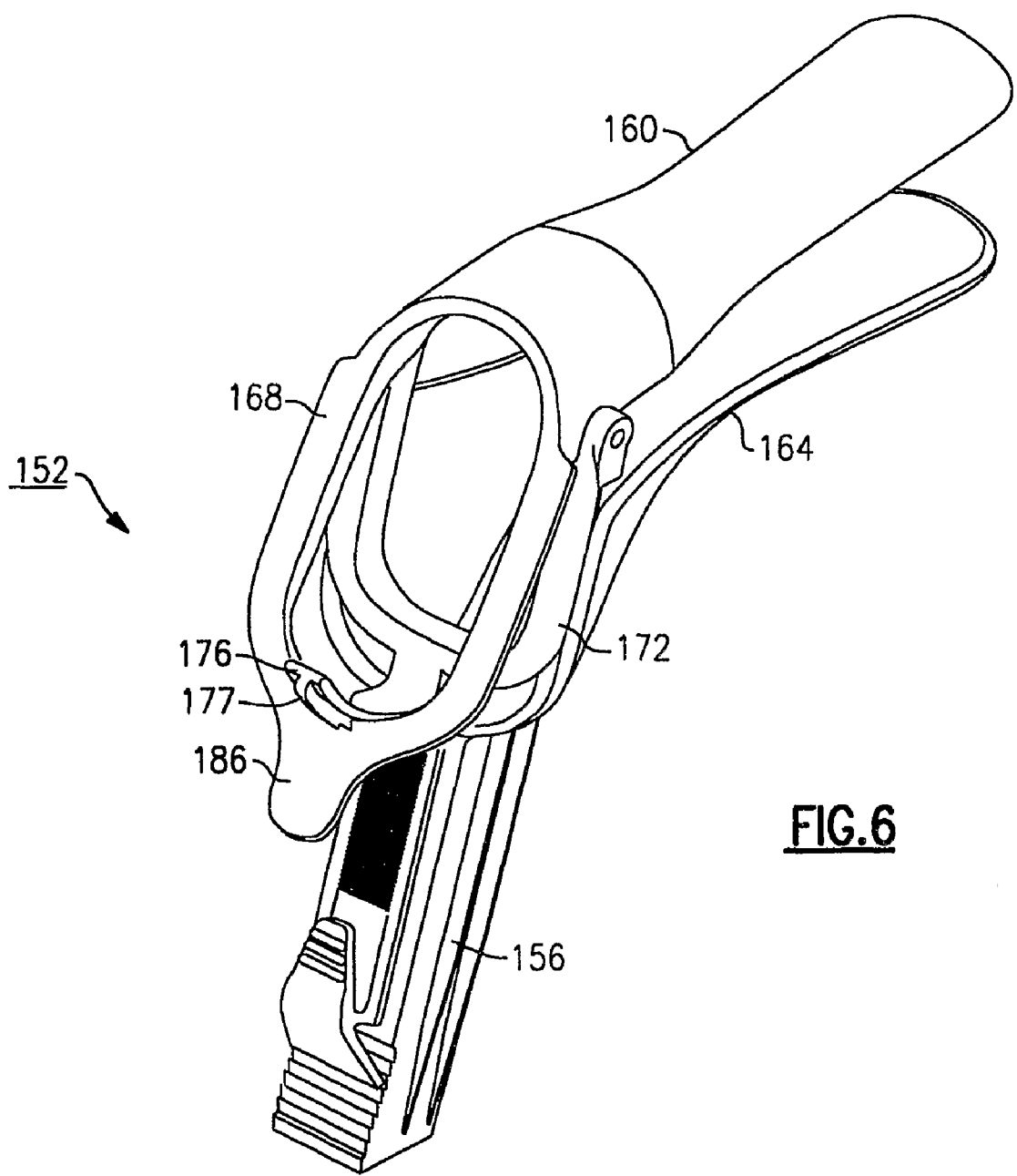
FIG. 6 is a rear perspective view of a vaginal speculum made in accordance with a variations of the second embodiment.
Figure 7:
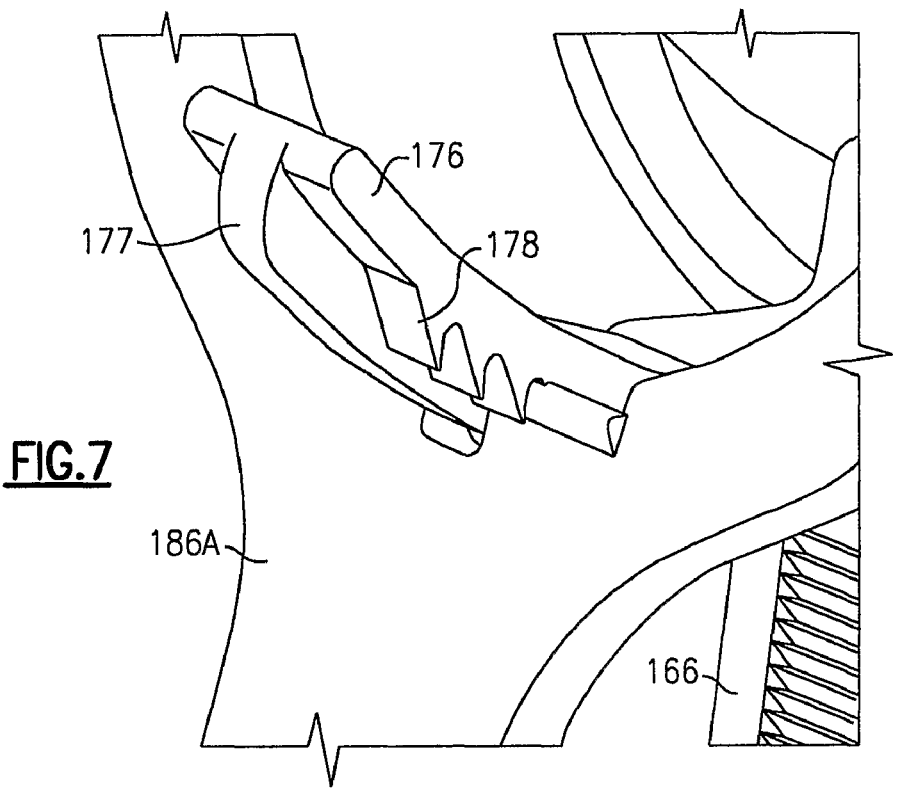
FIG. 7 is an enlarged partial view of the articulation mechanism of the vaginal speculum of FIG. 6.

Variations of the above articulation mechanism are possible. For example and as shown in FIGS. 6 and 7, the bottom tab 186A can be constructed without a shield member. The mechanism works in a similar manner as the preceding to produce quiet articulation per the passive mode, second form, by finger pressure on the proximal ridge 177 during articulation, causing flexing of the flexible projection 176. Releasing the finger pressure again causes a ratchet tooth to engage with the interior tab on the lever portion 168. Passive mode, first form, articulation is also possible—the user presses down on tab 186A without simultaneously applying pressure to the proximal ridge 177.

Figure 8:
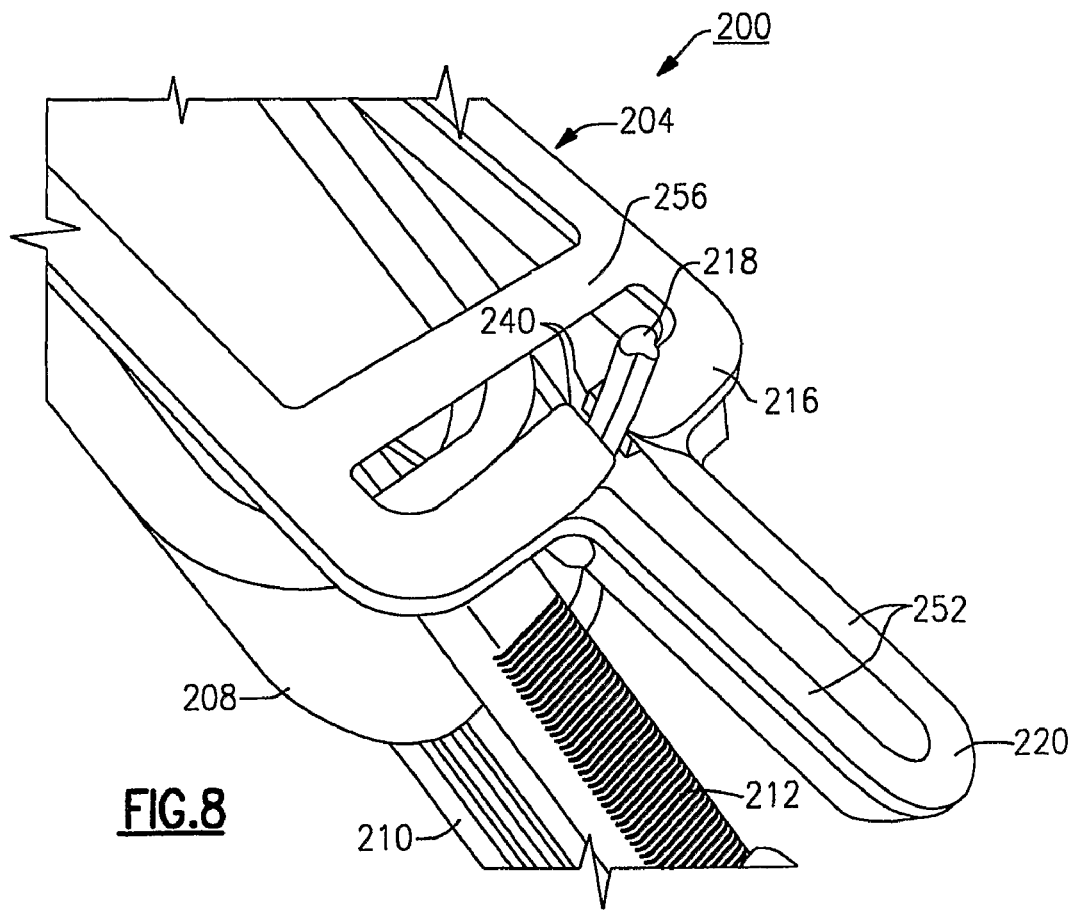
FIG. 8 is a partial rear perspective view of a vaginal speculum illustrating an articulation mechanism made in accordance with a third embodiment.
Figure 12:
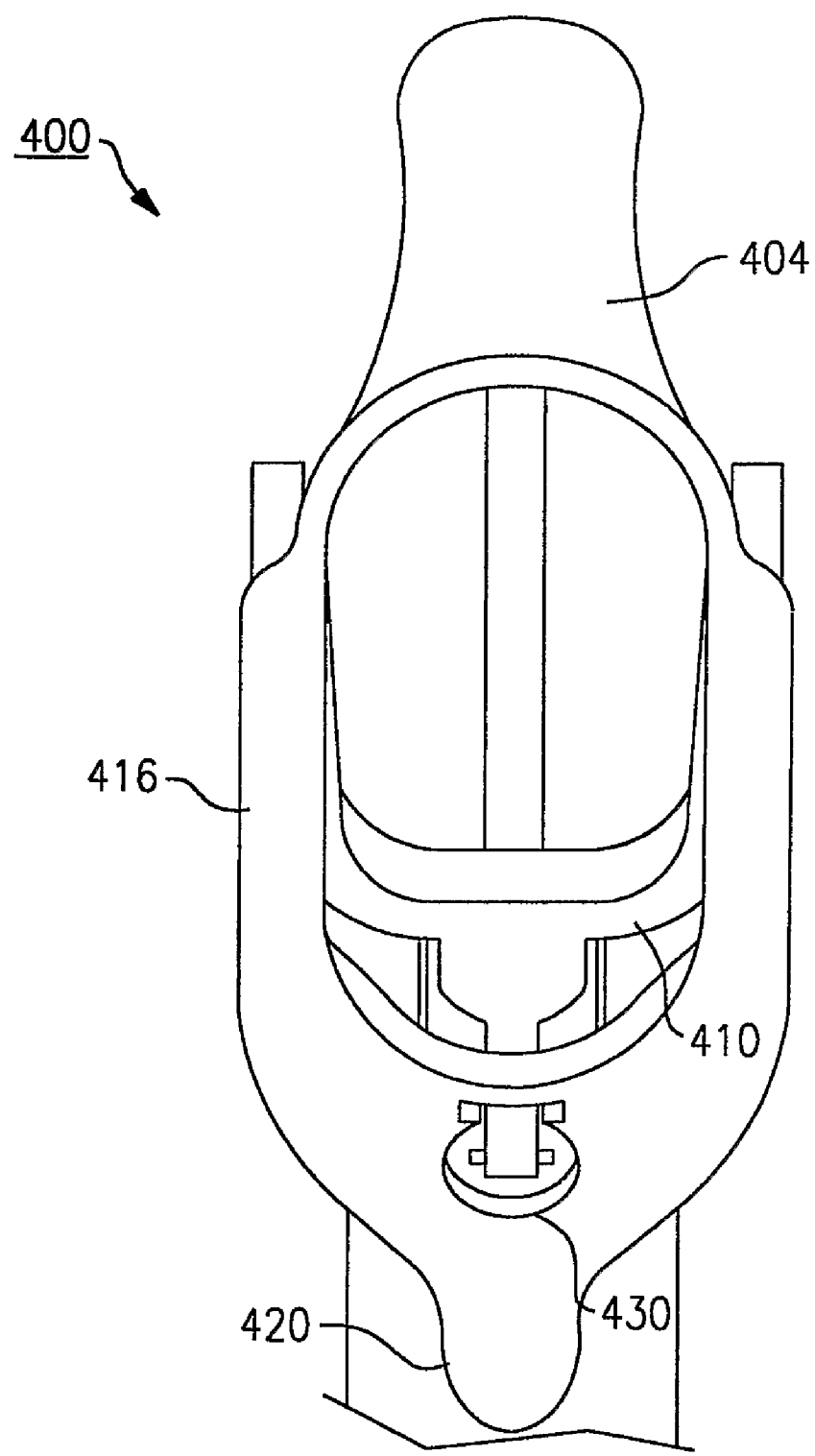
FIG. 12 is a rear view of a vaginal speculum having an articulation mechanism made in accordance with a fourth embodiment.
Figure 13:
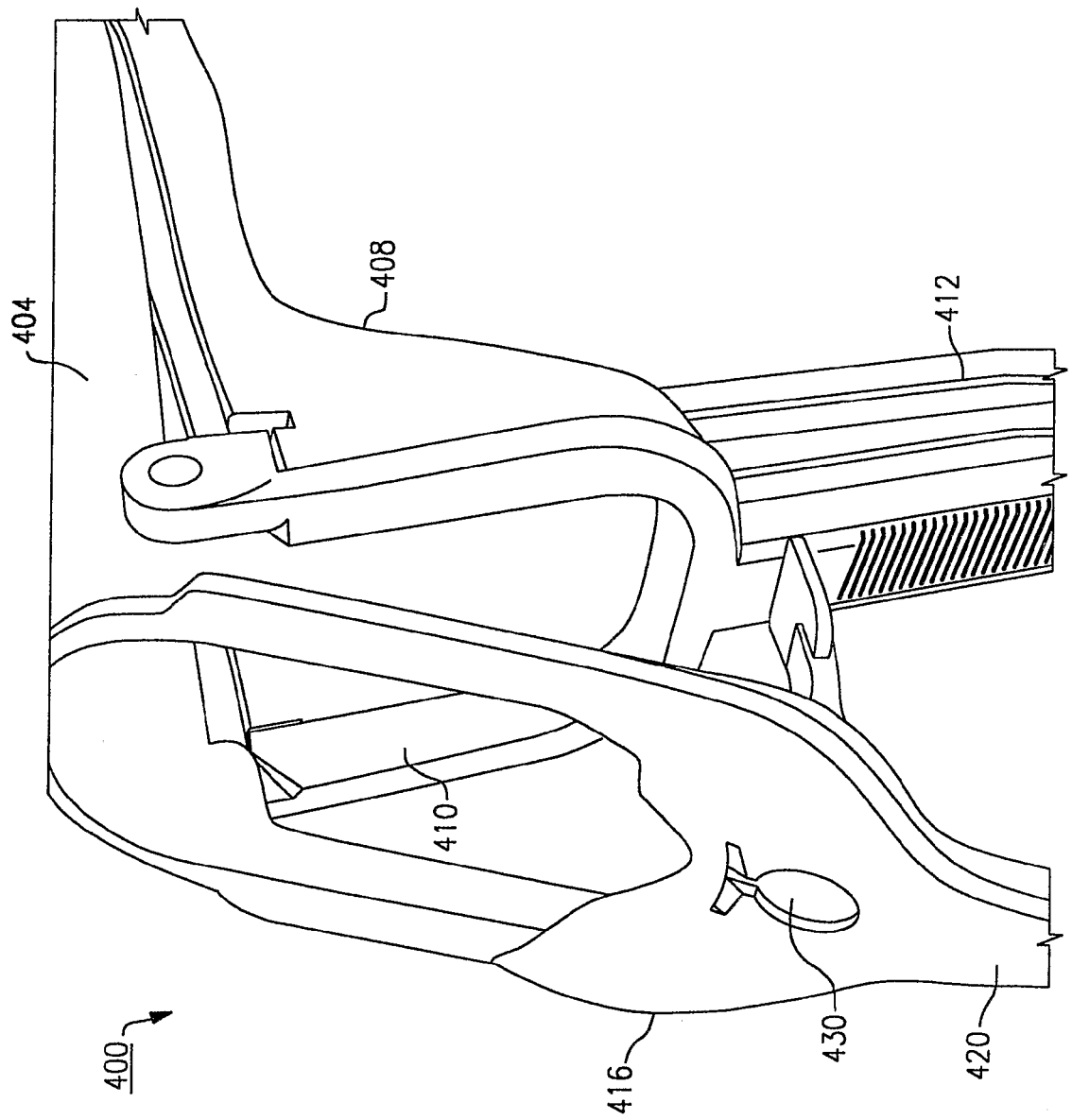
FIG. 13 is a rear perspective view of the vaginal speculum of FIG. 12, illustrating the articulation mechanism in a first position.
Figure 14:
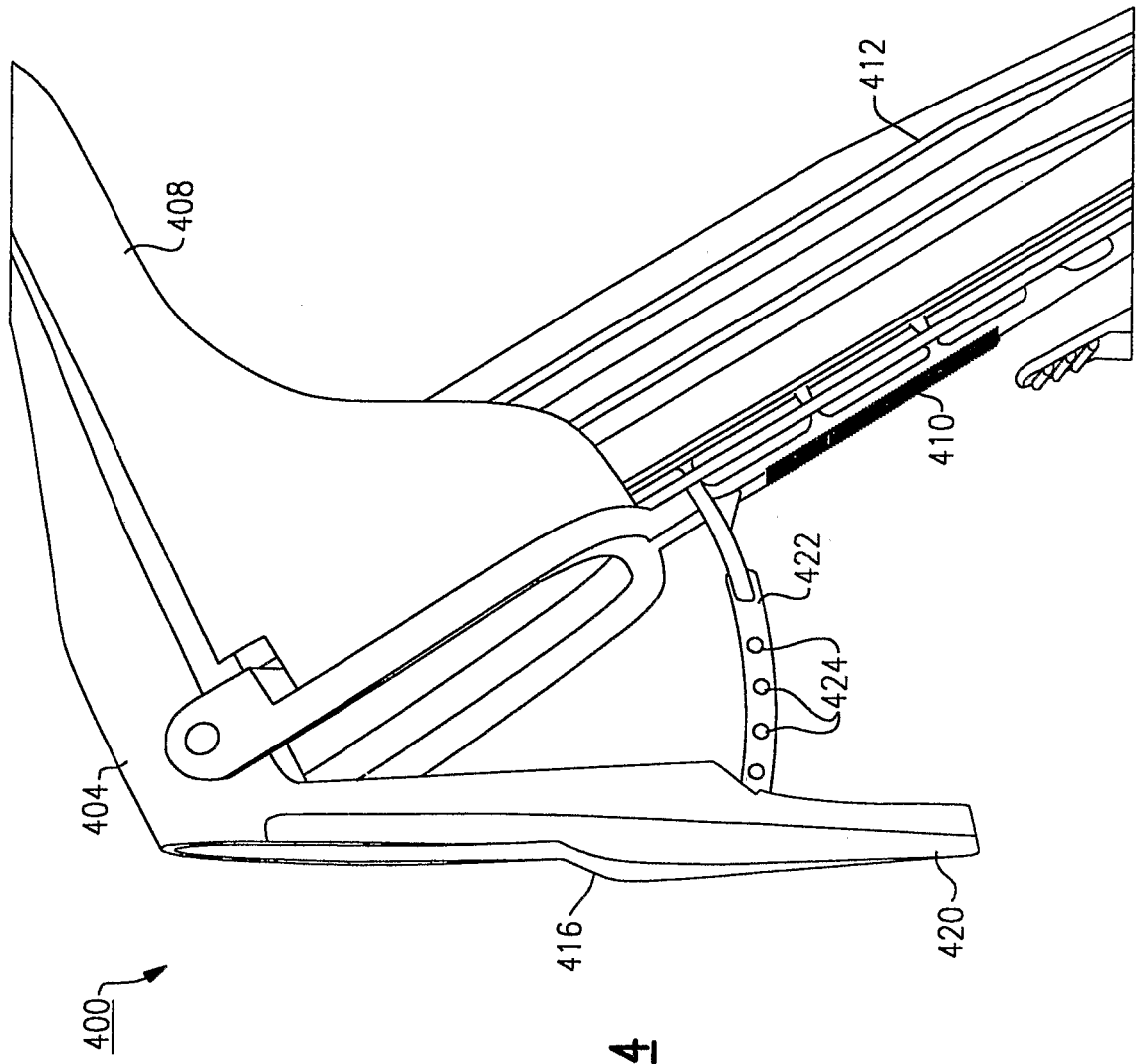
FIG. 14 is a perspective view of the speculum of FIG. 13.
Figure 15:
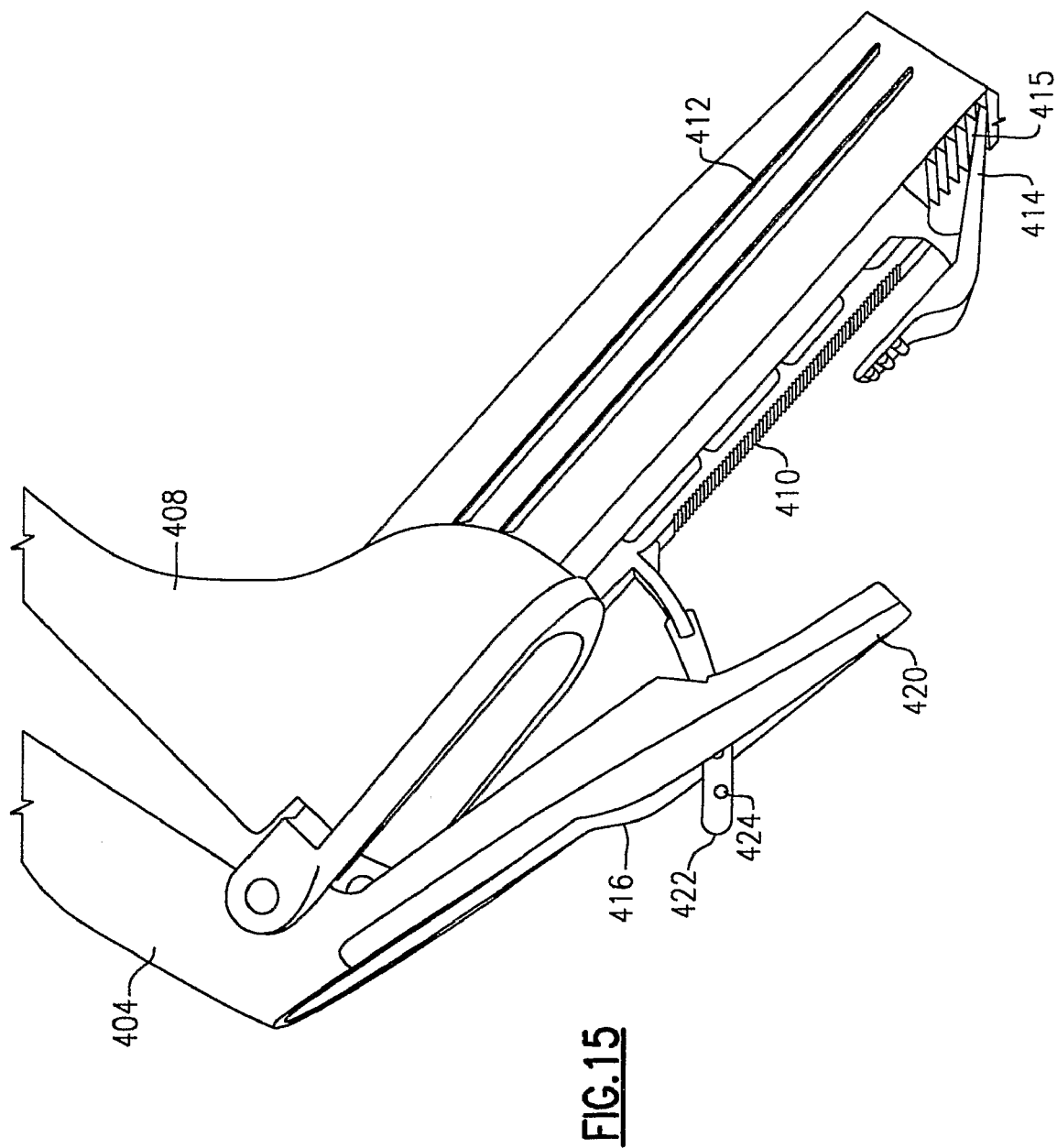
FIG. 15 is a partial side view of the speculum of FIGS. 12 and 13, illustrating the articulation mechanism in a second position.
Figure 16:
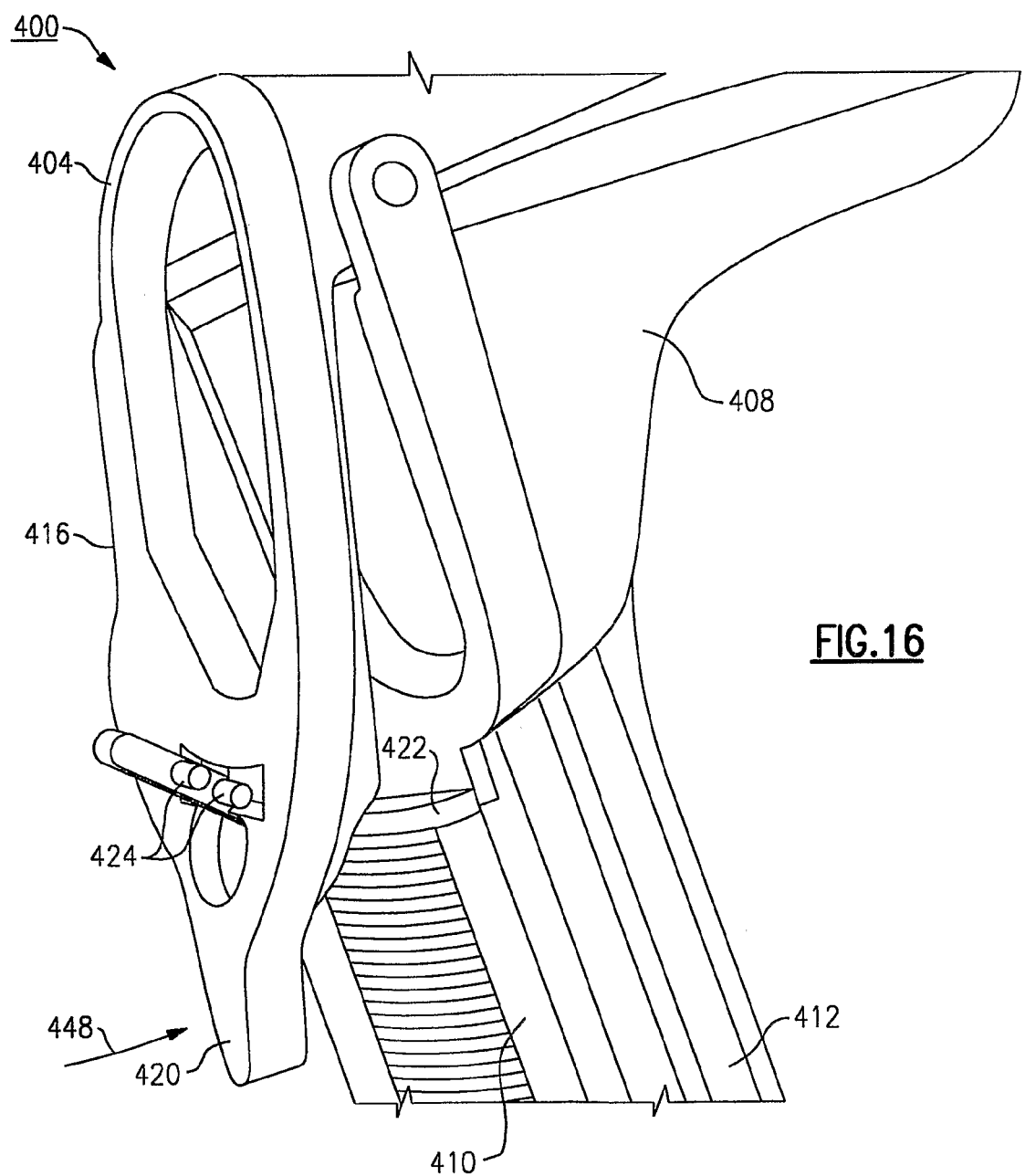
FIG. 16 is a rear perspective view of the speculum of FIG. 15.

Referring to FIGS. 8-10, there is shown a blade articulation mechanism for a vaginal speculum 200 made in accordance with a third embodiment. In this instance, the construction of the lower blade member of the speculum 200 is unchanged and therefore is identical to that depicted and previously described in FIG. 1. The speculum 200 also includes, as in the preceding, a slide member 212 that permits pivotal attachment of the upper blade member 204, the slide member being attached to a proximal end of the upper blade member at one end and within a vertical slot that is formed in a handle portion 210 of the speculum at the remaining end. The slide member 212 further includes a single tooth that engages with a set of teeth provided on the proximal side of the handle portion 210 for permitting elevation (translation) of the attached upper blade member 204.

The changes to the design of the speculum 200 for purposes of the herein described articulation mechanism relate to the design of the downwardly depending lever portion 216 of the upper blade member 204, as well as to the outwardly extending curved arm 218 of the slide member 212.

According to this embodiment, the lever portion design is varied to include at least one pair of opposing side tongues 240 through which the curved outwardly extending arm 218 of the slide member 212 passes in lieu of an engagement tooth as previously described. Only a single pair of side tongues 240 is shown in this embodiment. The side tongues 240 are disposed above the tab 220 and above the plane of the lever portion 216. The side tongues 240 are spaced laterally at a distance that is less than the width of the curved arm 218 such that the side tongues squeeze the curved arm between them. Consequently, when the tab 220 is depressed, the side tongues 240 move both up and away from the curved arm, thereby allowing relative motion between the curved arm and the lever portion 216 of the upper blade member 204. When the tab 220 is released and a load from the patient is applied to the speculum's upper and lower blade members 204, 208, the side tongues 240 move down and toward one another, thereby pinching the curved arm 218 between the opposing side tongues. Since the side tongues 240 can pinch the curved arm 218 at any location, the embodiment operates in a continuous rather than in a discrete manner. The operation is that of passive mode, second mode, as defined hereinabove.

The lever portion 216 of the upper blade member 204, according to this embodiment, is configured to permit the above-described motion to take place. Specifically, the lever portion 216 of the upper blade member 204 is provided with a pair of flexible parallel spaced legs 252 that twist during motion of the two opposing side tongues 240. A tie plate 256 prevents the spaced legs 252 from moving apart during this motion, the plate also flexing in order to permit the motion. Both the spaced legs 252, as well as the tie plate 256, produce a preload engagement force between the opposing side tongues 240 and the curved arm 218. During depression of the lever portion 216 via tab 220, this engagement force is reduced in that the side tongues 240 tend to move away from the curved arm 218. During use under load from the upper and lower blade members 204, 208, the engagement force is increased due to the above-noted pinching effect.

Disengagement (i.e., closing of the upper blade member 204) is accomplished in the same manner, as conventionally known. Pressure applied to the curved arm 218 towards the tie plate 256 of the lever portion 216 disengages the side tongues 240 from the curved arm 218. The tie plate 256 acts, according to this embodiment, as a stop for this displacement.

A variation to the preceding design is illustrated in FIG. 9. For purposes of this discussion, similar parts are labeled with the same reference numerals for the sake of clarity. In this variation, the curved arm 278 is constructed with an integral flange 282 extending along most of the length thereof and above the curved arm 218, FIG. 8. The principle of the articulation mechanism is the same as that of the preceding; however, the flange provides additional stiffening of the curved arm 278 in bending in order to facilitate disengagement of the curved arm from the side tabs 240 of the lever portion 216, the flange further providing a stop to prevent the curved arm from excessively moving too far proximally (i.e., towards the user). Operation remains continuous in this embodiment and passive mode, second form.

Referring to FIG. 11, an alternative variation of an articulation mechanism for the form of design utilizes a curved arm 318 having a series of lateral undulations 322. The undulations 322 according to the depicted design are configured so as to provide a plurality of preferred pinch regions 325 for the opposing side tongues 240 of the lever portion 216. With such a configuration, the engagement between the side tongues 240 and the curved arm 318 would not be continuous, but the articulation mechanism would be less likely to "slip", as opposed to the preceding continuous version described herein.

Referring to FIGS. 12-17, a fourth embodiment of an articulation mechanism for a vaginal speculum 400 is herein described. According to this embodiment, the design of the lower blade member 408 is that described in FIG. 1. As in the embodiment of FIG. 1, the slide member 410 is pivotally attached to the proximal end of the upper blade member 404 and elevation of the upper blade member is permitted by means selective engagement of a single tooth 414 of the slide member 410 with a set of serrated ratchet teeth 415 formed on the proximal end of the handle portion 412, the latter features being depicted in FIG. 15.

The significant changes made according to this embodiment are to the lever portion 416 of the upper blade member 404 and the outwardly extending curved arm 422 of the slide member 410, as now described. More specifically, the serrated ratchet teeth on the proximal side of the curved arm 422 are removed for purposes of this embodiment and a set of periodic protrusions 424 are symmetrically added to each of the lateral surfaces of the curved arm. In addition, the single engagement tooth on the lever portion 416 of the upper blade member 404 is removed in favor of a hole or opening 430 having a keyhole-like configuration, shown most clearly in FIG. 17. The larger portion 434 of the keyhole-like opening 430 is closest to the user, according to this embodiment, and is dimensioned such that the curved arm (and the lateral protrusions 424 thereupon) in its unloaded configuration pass through the opening without contact. The smaller or narrow portion 438 of the defined opening 430 is dimensioned such that the smaller cross sections of the curved arm 422 fit laterally, but the larger cross sections (i.e., those with lateral extensions 424) do not fit laterally therethrough.

Figure 17:
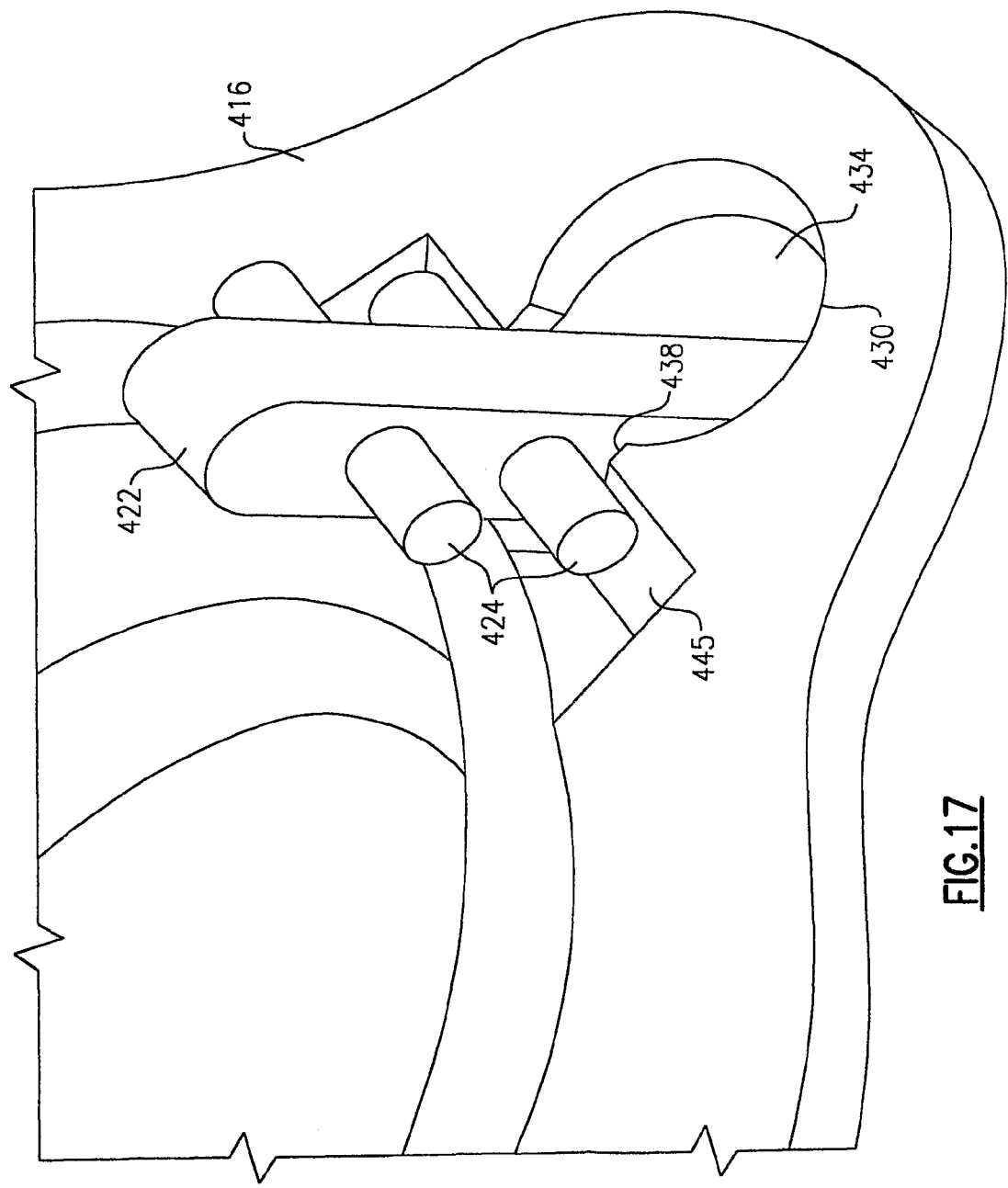
FIG. 17 is an enlarged view illustrating the interaction between the curved arm and the lever portion of the articulation mechanism of the speculum of FIGS. 12-16.

In operation as shown in FIG. 17, the user selects the articulation angle desired and then pushes upwardly on the curved arm 422. This upward push upon the curved arm 422 flexes the curved arm 422 into the narrow portion 438 of the keyhole-like opening 430 of the lever portion 416 such that a larger cross-section of the curved arm is above the plane of the keyhole. The curved arm 422 is retained in this position by a small protrusion (not shown) on the top surface of the tab 420 of the lever portion 416 or alternatively by a small ramp 445 provided at the distal (forward) end of the narrower portion 438 of the opening 430, but only while a blade-closing load from the patient is applied to the speculum 400. To close the upper blade member 404, the user presses down in the direction 448, see FIG. 16, slightly on the lever portion 416 of the upper blade member 404 at the tab 420. Doing so allows the curved arm 422 to return to its unflexed position, the unflexed position being shown in FIG. 12, which allows the larger (wider) portion 434 of the opening 430, FIG. 17, on the lever portion 416 to move past the lateral protrusions 424 of the curved arm 422, and thereby permits the blade articulation (i.e., angulation) to decrease. This embodiment operates in an active mode.

Figure 18:
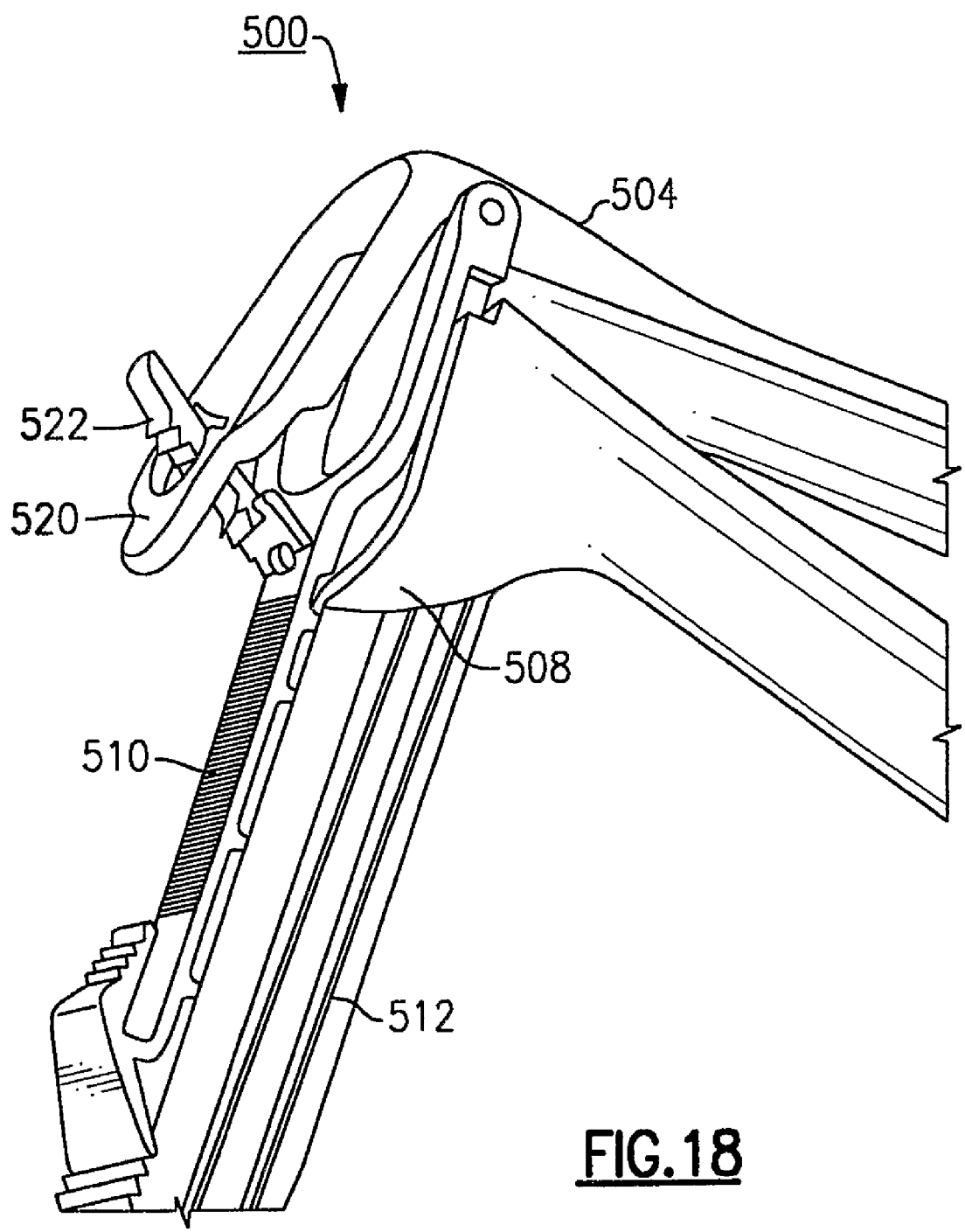
FIG. 18 is a rear perspective view of a vaginal speculum including an articulation mechanism in accordance with a fifth embodiment.
Figure 19:
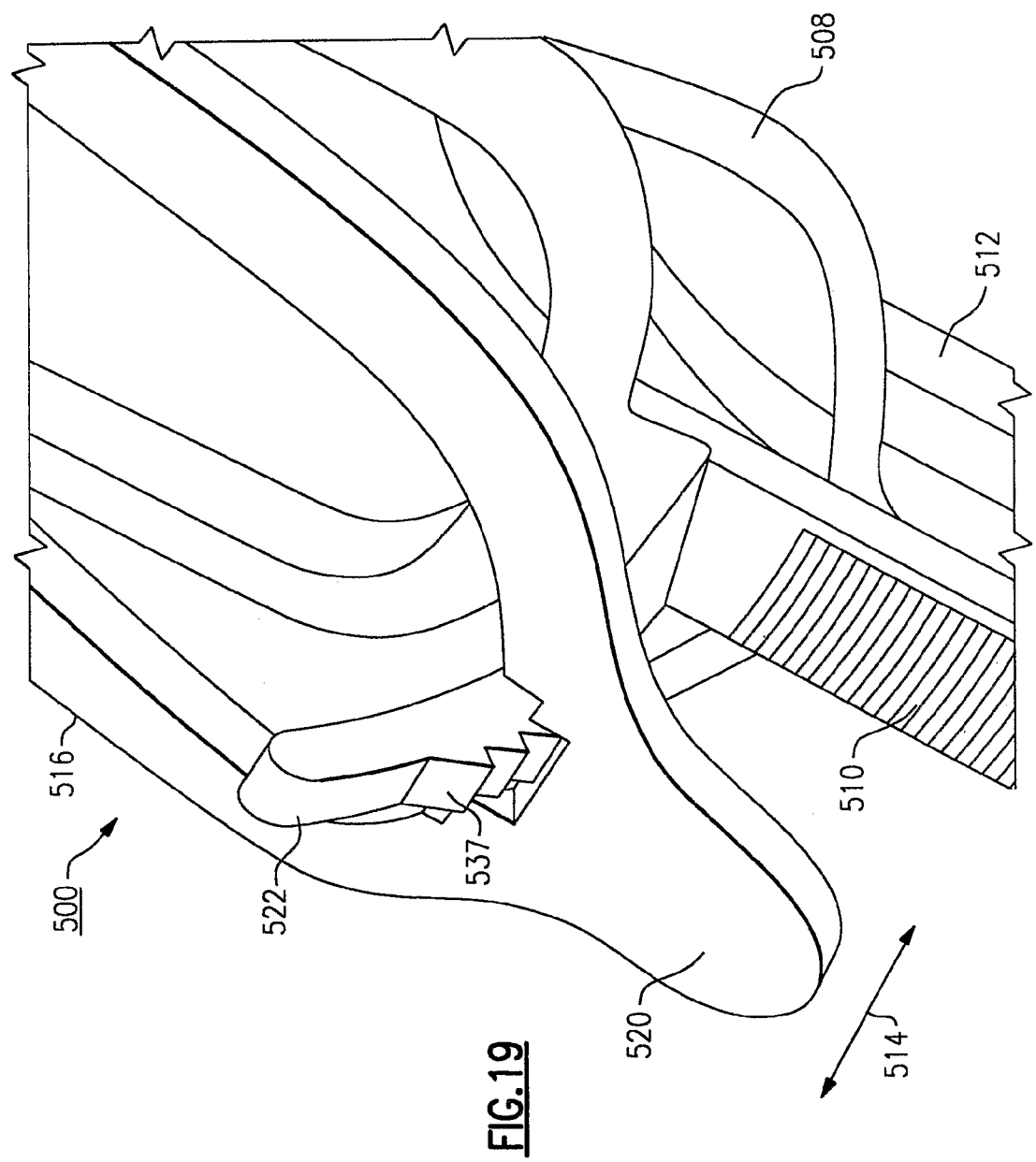
FIG. 19 is an enlarged view of the articulation mechanism of FIG. 18.

Referring to FIGS. 18 and 19, a vaginal speculum 500 having an articulation mechanism according to a fifth embodiment is herein described. According to this design, the structural components of the speculum 500 are also previously described including a top or upper blade member 504, a bottom or lower blade member 508, a slide member 510 that permits pivotal attachment of the upper blade member, and a handle portion 512 that depends from the lower blade member 508. The portions of the vaginal speculum 500 that are modified in comparison to those previously shown and described in FIG. 1 include the outwardly curved arm 522 and the lever portion 516 of the upper blade member 504. In this specific embodiment, the design of the curved arm 522 is not modified wherein the curved arm 522 includes a set of serrated ratchet teeth 537 on a proximal surface thereof. However and according to an alternative version, the teeth typically on the proximal surface of the curved arm can be removed in favor of a series of periodic protrusions, similar to those shown in FIGS. 12-17, that can be added symmetrically to the lateral surfaces of the curved arm 522. The engagement tooth provided on the lever portion 516 of the upper blade member 504 is removed, such that the curved arm (and the protrusions (not shown) and/or teeth 537 provided thereupon) pass through the tab 520 of the lever portion 516 of the upper blade member 504 without contact. The tab 520 of the lever portion 516 is configured such that moving the lever portion laterally in either direction, shown by arrows 514, causes the tab 520 to engage the lateral protrusions (not shown) or the teeth 537 provided on the proximal surface of the curved arm 522. It should be noted in passing that only a right-handed version of the apparatus is depicted in FIGS. 18 and 19, though it should be readily apparent that the tab 520 can be constructed to permit left-handed or both right and left handed operation.

In operation, which is active mode, as defined hereinabove, the lever portion 516 is first selectively adjusted by the user to select the articulation angle desired. The user then pushes laterally on the tab 520 of the lever portion 516, per an arrow 514. This lateral push flexes the lever portion 516 laterally such that the tab 520 engages one of the teeth 537 of the curved arm 522. The lever portion 516 is retained in this position by the engaged one of the teeth 537 of the curved arm 522, but only while a blade-closing force from the patient is being applied to the speculum 500. To close the upper blade member 504, the user presses down slightly on the tab 520. Doing so allows the lever portion 516 to return to its unflexed position, disengages the tab 520 from the one of the teeth 537, and allows the lever portion to move relative to the curved arm 522, thereby permitting the blade articulation (angulation) to decrease.

Figure 20:
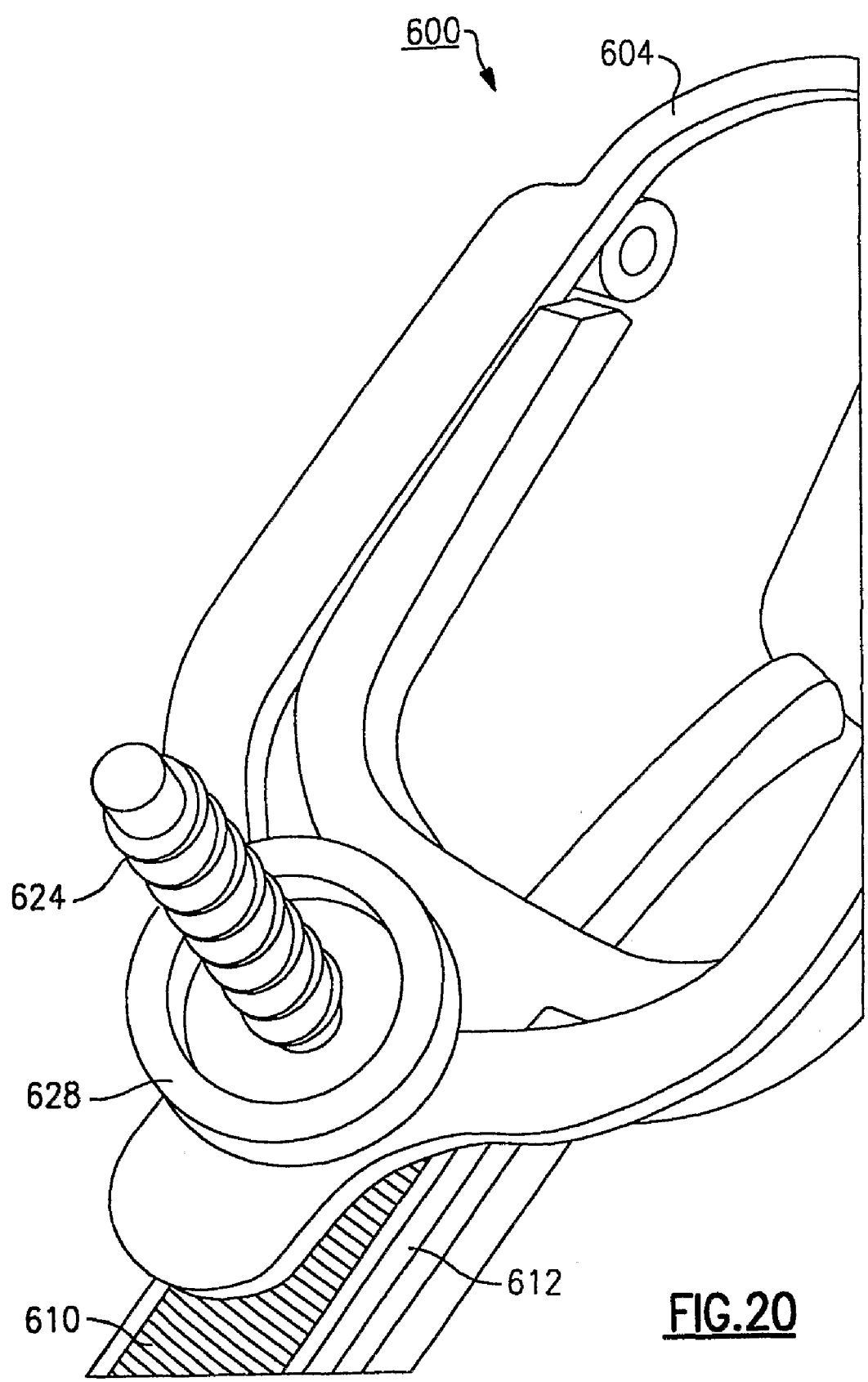
FIG. 20 is a rear perspective view of a vaginal speculum including an articulation mechanism in accordance with a sixth embodiment.
Figure 21:
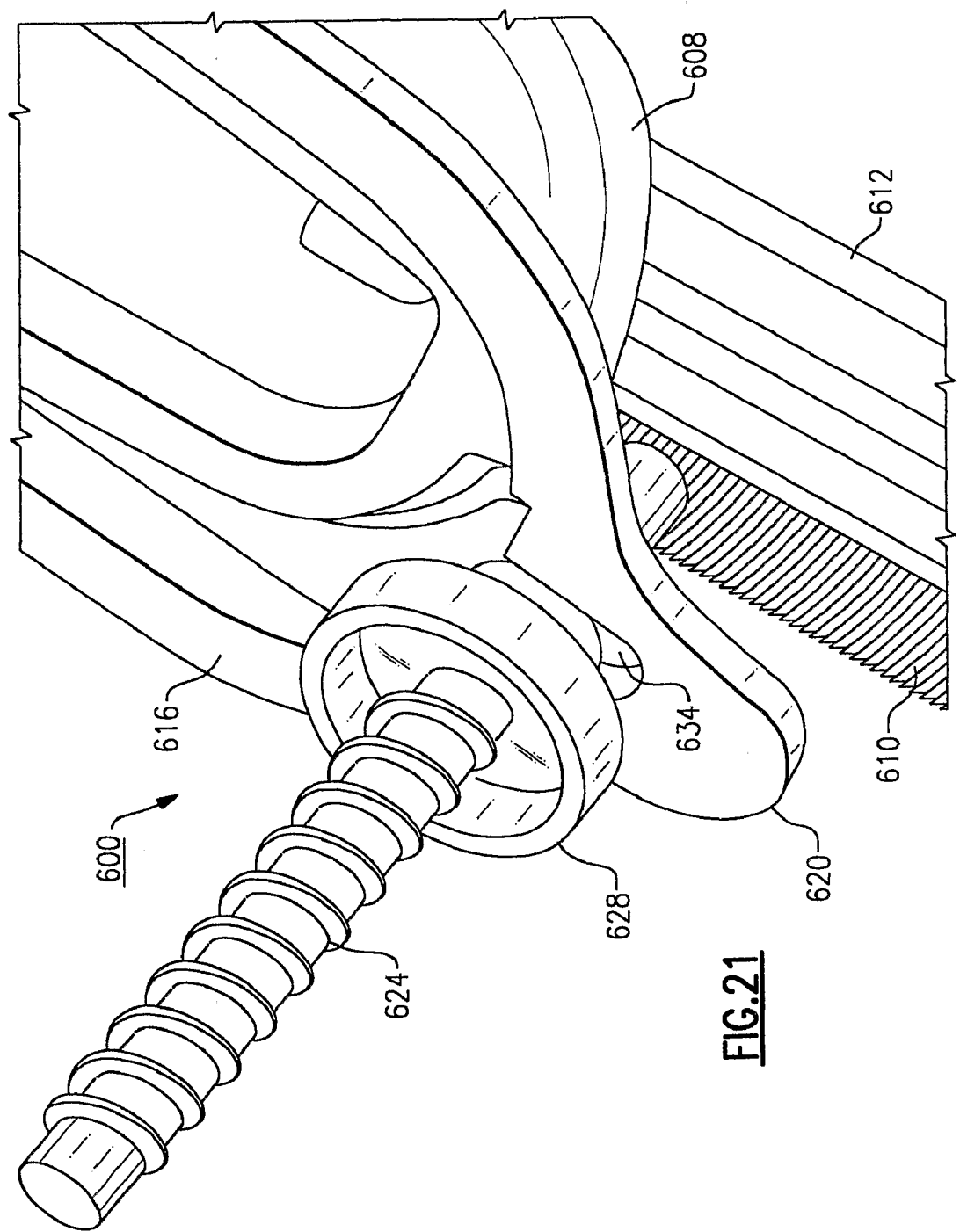
FIG. 21 is an enlarged view of the articulation mechanism depicted in FIG. 20.

Referring to FIGS. 20 and 21, there is described an articulation mechanism for a vaginal speculum 600 according to a sixth embodiment. As in each of the preceding embodiments, the speculum 600 includes a top or upper blade member 604, a bottom or lower blade member 608, a slide member 610 enabling pivotal attachment of the upper blade member 604, and a depending handle portion 612. According to this embodiment, those components that have been modified include the outwardly curved arm, which is replaced herein, and the downwardly depending lever portion 616 of the upper blade member 604.

According to this embodiment, which operates in an active mode, the curved arm is replaced by an elongated member 624 having a screw thread and an adjustable screw cap 628 that is axially movable along the screw thread. The elongated member 624 is mounted at one end to the slide member 610. This mounting can be via a pivot or, preferably the elongated member 624 can be part of the molded slide member 610. The mounting of the elongated member 624 permits the member to be lifted or flexed vertically at its free end. The adjustable screw cap 628 has a substantially circular cross section and a center opening with an internal screw thread, enabling rotation and corresponding axial translation thereof relative to the screw thread. The adjustable screw cap 628 includes a surface on a distal end thereof to facilitate engagement with the lever portion 616 of the upper blade member 604 to enable selective articulation. The downwardly extending lever portion 616 of the upper blade member 604 includes a slotted engagement portion 634 into which the elongated member 624 is raised and lowered, the distal surface of the adjustable screw cap 628 fitting against the slotted engagement portion. When the elongated member 624 is engaged in the slotted engagement portion 634, the degree of movement of the adjustable screw cap 628 along the defined screw thread provides the desired angulation of the upper blade member 604. To close the upper blade member 604, the user presses up on the elongated member 624. This causes the elongated member 624 to move out of the slotted engagement portion 634 and allows the lever portion 616 of the upper blade member 604 to move relative to the elongated member, thereby permitting articulation (angulation) of the upper blade member 604 to decrease.

PARTS LIST FOR FIGS. 1-21

20 vaginal speculum
24 top or upper blade member
28 bottom or lower blade member
32 hollow handle portion
35 vertical slot
36 lever portion
39 engagement tooth
40 slide member 42 upper yoke section
44 curved arm
48 serrated ratchet teeth
50 tooth, single engagement
54 serrated ratchet teeth, handle portion
60 tab
100 vaginal speculum
110 top blade member
114 lower blade member
116 handle portion
117 teeth
118 lever portion
122 opening
126 slide or yoke member
128 tooth
130 curved arm
134 engagement surface, ramped
137 serrated ratchet teeth
138 lever extension
142 engagement portion
144 flat portion, lever extension
146 curved extension
150 vaginal speculum assembly
152 disposable speculum
154 reusable illumination assembly
156 hollow handle portion
158 receiving cavity
160 upper or top blade member
164 lower or bottom blade member
166 slide member
168 lever portion
172 upper portion or yoke
176 flexible projection
177 proximal ridge
178 ratchet teeth
182 opening
186 bottom tab
186A bottom tab
188 shield member
189 engagement end
200 speculum
204 upper or top blade member
208 lower or bottom blade member
210 handle portion
212 slide member
216 lever portion
218 curved arm
220 tab
240 side tongues
252 legs, spaced pair
256 tie plate
278 curved arm
282 flange, integral
318 curved arm
322 undulations
325 preferred pinch regions
400 speculum
404 upper blade member
408 lower blade member
410 slide member
412 handle portion
414 tooth
415 ratchet teeth, handle portion
416 lever portion
420 tab
422 curved arm
424 protrusions, lateral
430 opening
434 larger portion, opening
438 narrow portion, opening
445 ramp, opening
448 direction
500 speculum
504 top or upper blade member
508 bottom or lower blade member
510 slide member
512 handle portion
514 arrows
516 lever portion
520 tab
522 curved arm
537 tooth, ratchet
600 speculum
604 upper blade member
608 lower blade member
610 slide member
612 handle portion
616 lever portion
624 elongated member
628 adjustable screw cap
634 slotted engagement portion

We claim:

1. A vaginal speculum comprising:
an upper blade member having a downwardly extending lever portion;
a lower blade member; and
a slide member interconnecting said upper blade member and said lower blade member and permitting relative movement therebetween; and
an articulation mechanism in which said lever portion includes an engagement tooth that is selectively engageable with an engagement feature of said slide member for selectively enabling the upper blade member and lower blade member to be angularly articulated along a length of said slide member engagement feature, said articulation mechanism including at least one engagement element that is selectively engageable by a user to provide engagement between a curved arm of said slide member having said engagement feature and the engagement tooth, said at least one engagement element being disposed on said lever portion and including a flexible projecting portion that when engaged by a user, causes said curved arm to be moved out of engagement with said lever portion and permits relative movement between said upper and lower blade members without requiring contact between said slide element engagement feature and said engagement tooth;
wherein articulation along the length is in one of two modes.

2. A vaginal speculum as recited in claim 1, wherein the articulation mechanism is configured for at least one passive mode and an active mode.

3. A vaginal speculum as recited in claim 1, wherein said slide member engagement feature includes a series of serrated teeth wherein movement of said engagement element in a first form of passive mode causes direct engagement of said engagement tooth with said series of serrated teeth and in which movement of said engagement element in a second form of passive mode causes a portion of said engagement element to engage said curved arm, permitting quiet angulation.

4. A vaginal speculum as recited in claim 3, wherein said slide member engagement feature further includes a proximal ridge onto which said engagement element engages in lieu of said series of serrated teeth in said second form of passive mode.

5. A vaginal speculum as recited in claim 3, wherein said first form of passive mode produces ratcheting operation over a discrete number of articulation positions and said second form of passive mode produces quiet operation over said discrete number of articulation positions.

6. A vaginal speculum as recited in claim 1, wherein said slide member engagement feature including a series of serrated teeth disposed along a bottom surface of said curved arm and an axial ridge disposed along the bottom surface of said curved arm, wherein engagement of said axial ridge by a user permits said curved arm to be moved out of said engagement portion of said lever portion to permit selective engagement of one of said series of said serrated teeth with said lever portion to effect angular articulation between said upper blade and said lower blade members.

7. A vaginal speculum comprising:
an upper blade member;
a lower blade member;
a slide member interconnecting said upper blade member and said lower blade member to permit relative movement between said upper blade member and said lower blade member, said slide member including a rearwardly extending flexible curved arm; and
an articulation mechanism including a lever portion extending from said upper blade member, said lever portion including an engagement portion, said engagement portion having an aperture sized to engage said curved arm, said curved arm having a plurality of protrusions wherein engagement and movement of said lever portion permits said curved arm to pass through said aperture without contact therewith along a length of the plurality of protrusions to produce angulation between said upper blade member and said lower blade member and in which subsequent movement of said curved arm causes said engagement portion to lock into engagement with at least one protrusion of said curved arm, said at least one engagement portion including a flexible projecting portion that when engaged by a user, causes said flexible curved arm to be moved out of engagement with said lever portion and permits relative movement between said upper and said lower blade members without requiring contact between said plurality of protrusions and said engagement portion.

8. A vaginal speculum comprising:
an upper blade member;
a lower blade member;
a slide member interconnecting said upper blade member and said lower blade member to permit relative movement between said upper blade member and said lower blade member; and
an articulation mechanism including a lever portion downwardly extending from a proximal end of said upper blade member, said lever portion including an engagement portion sized for engaging a rearwardly extending flexible curved arm of said slide member, said flexible curved arm including a plurality of spaced engagement surfaces wherein engagement and movement of said lever portion in a first direction causes said curved arm to pass through said engagement portion creating angulation between said upper blade member and said lower blade member without contacting said engagement surfaces along a length of the plurality of spaced engagement surfaces and in which movement of said lever portion in a second direction causes engagement between said lever portion and an engagement surface of said curved arm to lock the angulation position, said engagement portion including a flexible projecting portion that when engaged by a user, causes said flexible curved arm to be moved out of engagement with said lever portion and permits said relative movement between said upper and said lower blade members without requiring contact between engagement surfaces and said engagement portion.

9. A vaginal speculum comprising:
a lower blade member having a handle portion;
an upper blade member having a downwardly extending lever portion;
a slide member interconnected to said upper blade member and said lower blade member and permitting relative movement between said upper blade member and said lower blade member, said slide member including a rearwardly extending curved arm having a series of serrated teeth, said lever portion further including an engagement tooth that is selectively engageable with one of said serrated teeth to selectively define an angular spacing between the upper and lower blade members, said lever portion including means for selectively moving said lever portion relative to said curved arm to select said angular blade spacing without direct engagement between the engagement tooth of said lever portion and the serrated teeth of said curved arm; and
at least one engagement element that is selectively engageable by a user to provide engagement between the curved arm and the engagement tooth,
wherein said at least one engagement element is disposed on said lever portion, said at least one engagement element including a flexible projecting portion that when engaged by a user, causes said flexible curved arm to be moved out of engagement with said lever portion and permits relative movement between said upper and said lower blade members without requiring contact between said series of serrated teeth and said engagement tooth.

10. A vaginal speculum as recited in claim 9, wherein said slide member includes an engagement member enabling said slide member to move in relation to said handle portion without requiring contact between engagement teeth of said handle portion and an engagement tooth of said slide member.

11. A vaginal speculum comprising:
an upper blade member including a downwardly extending lever portion and a bottom tab;
a lower blade member; and
a slide member pivotally interconnecting the proximal end of said upper blade member and said lower blade member, wherein said lever portion includes at least one lever engagement feature and said slide member includes an outwardly extending curved arm having a least one lateral arm engagement feature engaged by said lever engagement feature for permitting angular articulation of said upper and lower blade members,
wherein said at least one lever engagement feature includes at least one pair of spaced side tongues, said at least one pair of side tongues having a spacing that is smaller than the width of said curved arm, and
wherein said lever portion includes a pair of flexible spaced legs that twist during motion of the at least one pair of side tongues.

12. A vaginal speculum as recited in claim 11, wherein said at least one lateral arm engagement feature includes a plurality of spaced lateral undulations.

13. A vaginal speculum as recited in claim 12, wherein said undulations define pinch regions for said at least one lever engagement feature.

14. A vaginal speculum as recited in claim 13, wherein said at least one lever engagement feature includes at least one pair of side tongues, said at least one pair of side tongues having a spacing therebetween that is smaller than the width of said curved arm having said undulations.

15. A vaginal speculum as recited in claim 14, wherein said lever portion includes a pair of flexible spaced legs that twist during motion of the at least one pair of side tongues.

16. A vaginal speculum as recited in claim 14, wherein said bottom tab is acted upon by a user to move the at least one pair of side tongues into engagement with the at least one lateral arm engagement feature.

17. A vaginal speculum as recited in claim 14, wherein said outwardly extending curved arm is acted upon by a user to move said at least one pair of side tongues out of engagement with said at least one lever engagement feature.

18. A vaginal speculum as recited in claim 14, wherein said bottom tab is acted upon by a user to move the at least one pair of side tongues into engagement with the at least one lateral arm engagement feature.

19. A vaginal speculum as recited in claim 14, wherein said outwardly extending curved arm is acted upon by a user to move said at least one pair of side tongues out of engagement with said at least one lever engagement feature.

20. A vaginal speculum as recited in claim 11, wherein said at least one lateral arm engagement feature includes a flange extending along substantially the length of said curved arm.

21. A vaginal speculum as recited in claim 11, wherein said engagement features enable continuous operation over a range of articulation position such that said blade members can be set selectively within a range of articulation positions.

* * * * *